United States Patent
Nakano et al.

(10) Patent No.: US 10,420,282 B2
(45) Date of Patent: Sep. 24, 2019

(54) FRUIT OR VEGETABLE PRODUCT HARVESTING APPARATUS AND FRUIT OR VEGETABLE PRODUCT HARVESTING METHOD

(71) Applicant: Sharp Kabushiki Kaisha, Sakai, Osaka (JP)

(72) Inventors: Takashi Nakano, Sakai (JP); Yoshihisa Adachi, Sakai (JP); Daiichiro Nakashima, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 185 days.

(21) Appl. No.: 15/649,678

(22) Filed: Jul. 14, 2017

(65) Prior Publication Data
US 2018/0042178 A1 Feb. 15, 2018

(30) Foreign Application Priority Data

Aug. 10, 2016 (MY) .......................... PI 2016001488

(51) Int. Cl.
*A01D 46/30* (2006.01)
*A01D 91/04* (2006.01)
(Continued)

(52) U.S. Cl.
CPC ............. *A01D 46/30* (2013.01); *A01D 46/00* (2013.01); *A01D 91/04* (2013.01); *G01N 21/314* (2013.01); *G01N 21/359* (2013.01); *G01N 21/3563* (2013.01); *G01N 21/84* (2013.01); *G01N 33/025* (2013.01); *G01N 2021/3155* (2013.01);
(Continued)

(58) Field of Classification Search
CPC ...... A01D 45/006; A01D 46/00; A01D 46/24; A01D 46/30; A01D 75/00; A01D 91/04; G01N 21/84; G01N 21/314; G01N 21/3563; G01N 21/359; G01N 33/025
USPC .......... 56/10.2 R, 10.5, 328.1; 460/134, 136; 700/213; 701/50
See application file for complete search history.

(56) References Cited

U.S. PATENT DOCUMENTS 4,843,561 A * 6/1989 Larson .................. A01D 46/24
209/587
5,426,927 A * 6/1995 Wang ..................... A01D 46/24
56/328.1
(Continued)

FOREIGN PATENT DOCUMENTS

JP 08-122250 A 5/1996
JP 2000-356591 A 12/2000
(Continued)

OTHER PUBLICATIONS

Bensaeed et al., "Oil palm fruit grading using a hyperspectral device and machine learning algorithm", IOP Conf. Series: Earth and Environmental Science 20 (2014), pp. 1-22.

*Primary Examiner* — Robert E Pezzuto
(74) *Attorney, Agent, or Firm* — Keating & Bennett, LLP

(57) ABSTRACT

A harvesting apparatus for a fruit or vegetable product includes a maturity determination device to determine a maturity level of the fruit or vegetable product; a harvester to harvest the fruit or vegetable product; a power source generator to drive the harvester; and a controller to determine whether or not to supply the power to the harvester based on a determination result on the maturity level provided by the maturity determination device.

16 Claims, 26 Drawing Sheets

(51) Int. Cl.
  *G01N 21/3563* (2014.01)
  *G01N 21/359* (2014.01)
  *G01N 21/84* (2006.01)
  *G01N 33/02* (2006.01)
  *A01D 46/00* (2006.01)
  *G01N 21/31* (2006.01)

(52) U.S. Cl.
  CPC ............... *G01N 2021/3177* (2013.01); *G01N 2021/8466* (2013.01)

(56) References Cited

U.S. PATENT DOCUMENTS

| | | | |
|---|---|---|---|
| 8,381,501 B2 * | 2/2013 | Koselka | A01D 46/30 56/10.2 A |
| 9,462,749 B1 * | 10/2016 | Jens | A01D 46/30 |
| 9,480,202 B2 * | 11/2016 | Pitzer | A01D 46/30 |
| 9,492,848 B1 * | 11/2016 | Davis | B07C 5/3422 |
| 9,789,518 B2 * | 10/2017 | Iino | B07C 5/3422 |
| 2006/0150602 A1 * | 7/2006 | Stimmann | A01D 46/30 56/10.5 |

FOREIGN PATENT DOCUMENTS

| | | |
|---|---|---|
| JP | 2015-046162 A | 3/2015 |
| JP | 5810494 B2 | 11/2015 |
| WO | 2006/014974 A2 | 2/2006 |
| WO | 2012/074372 A2 | 6/2012 |

\* cited by examiner

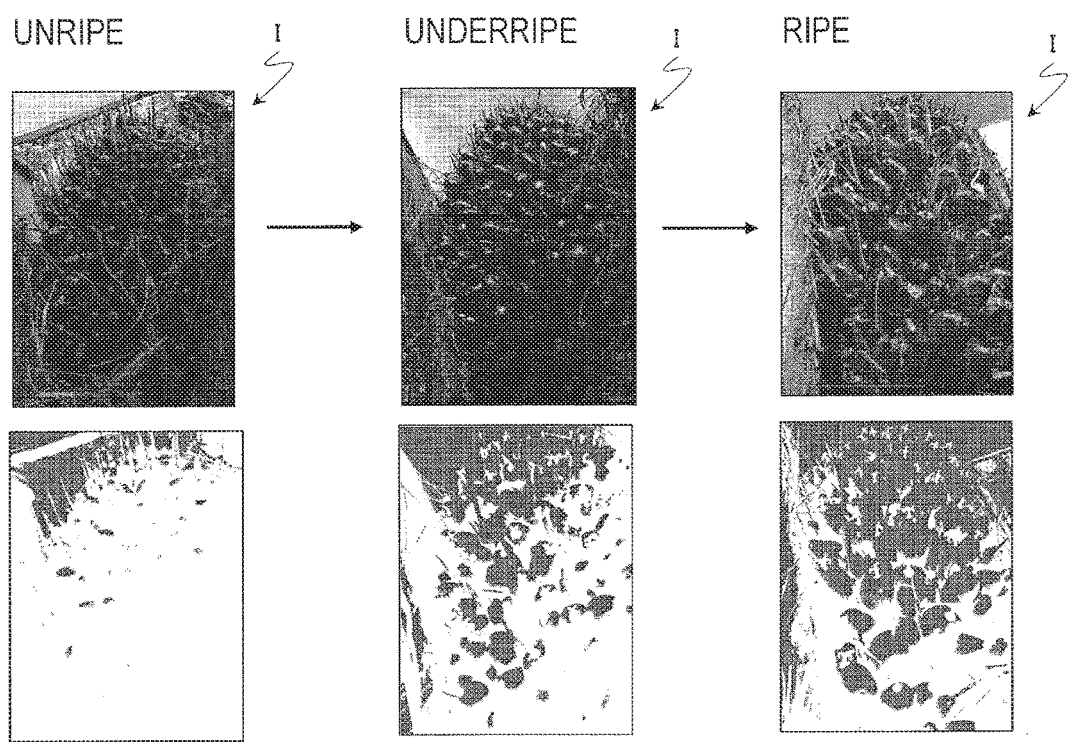

FIG.13A
(a)
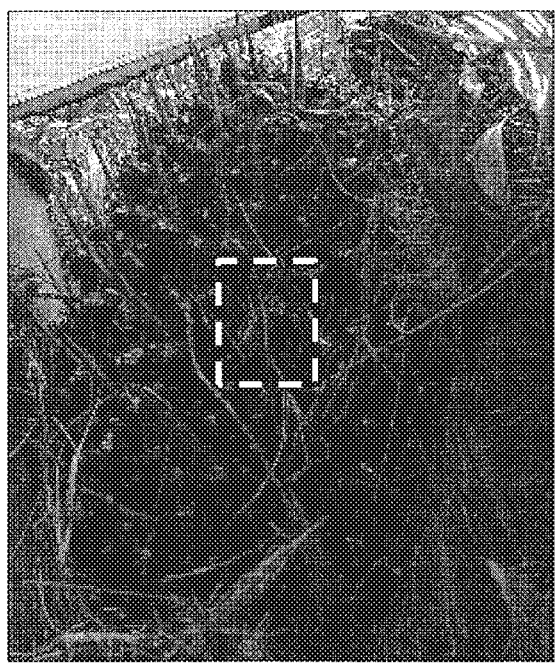
(b)
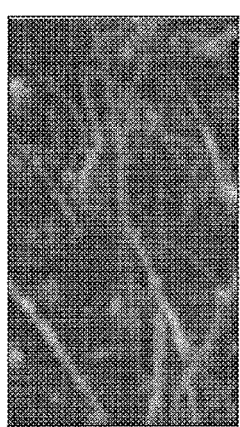
(c)

FIG.13B
(a)
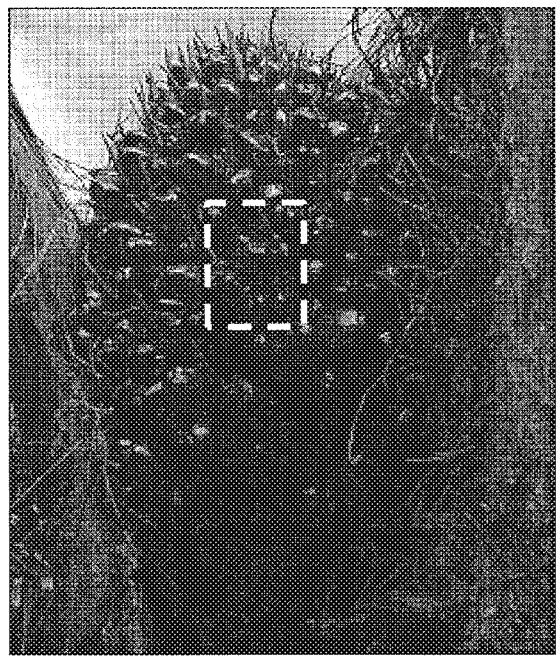
(b)
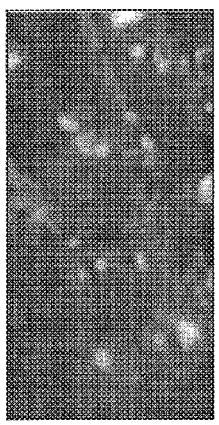
(c)

FIG.13C
(a)
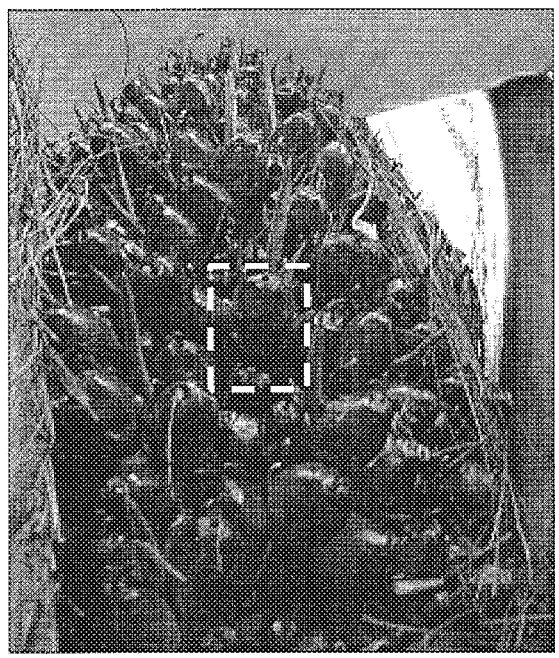
(b)　　　　　(c)
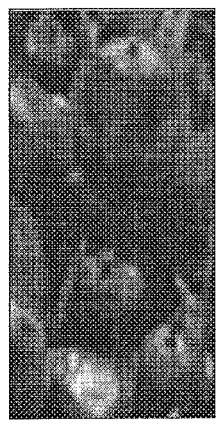
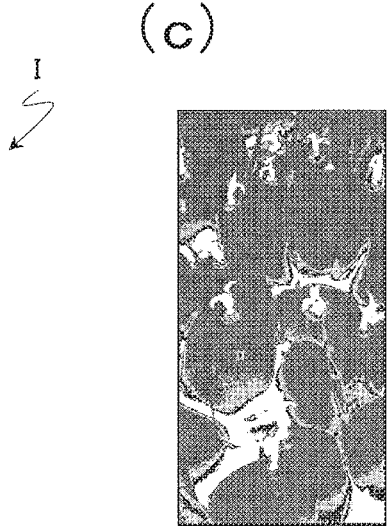

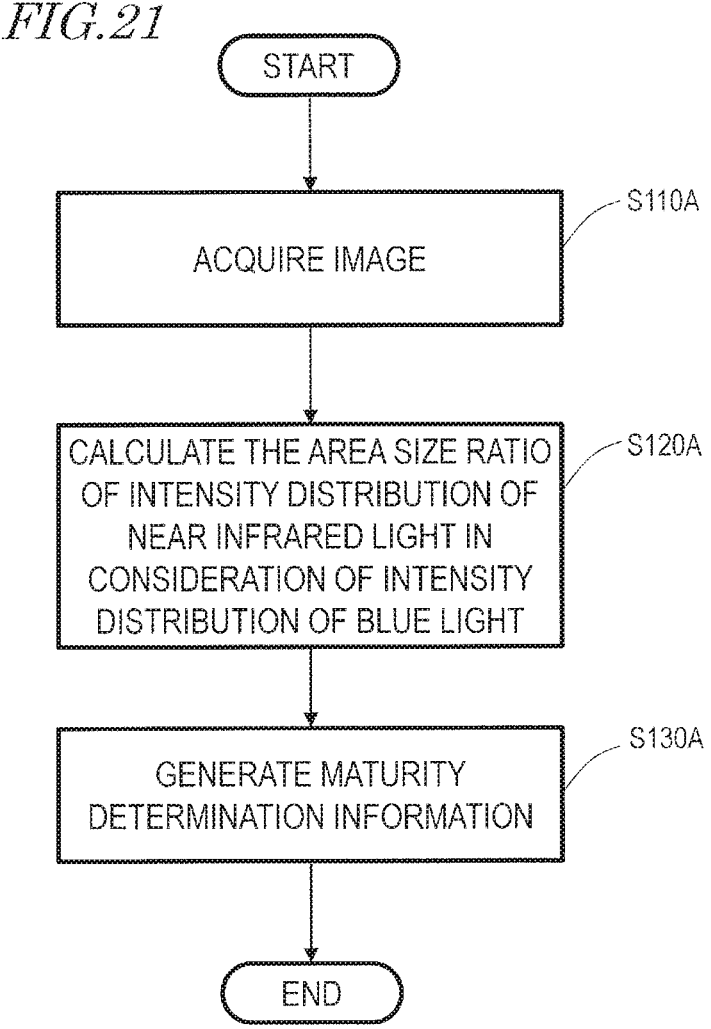

FIG.22A
(a)
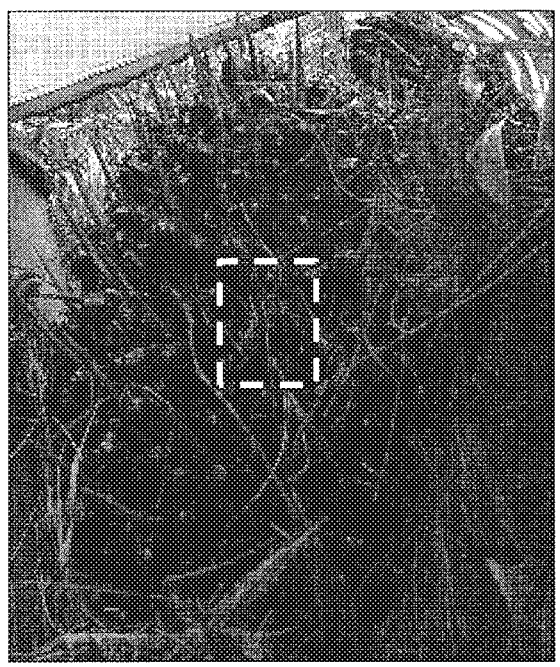
(b)
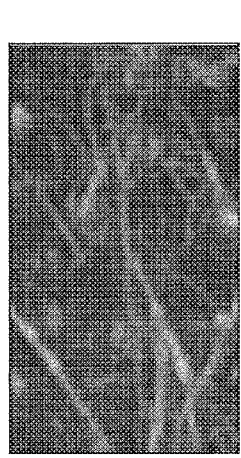
(c)
(d)
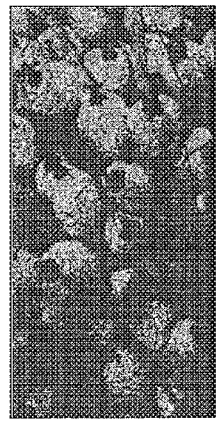

FIG.22B
(a)
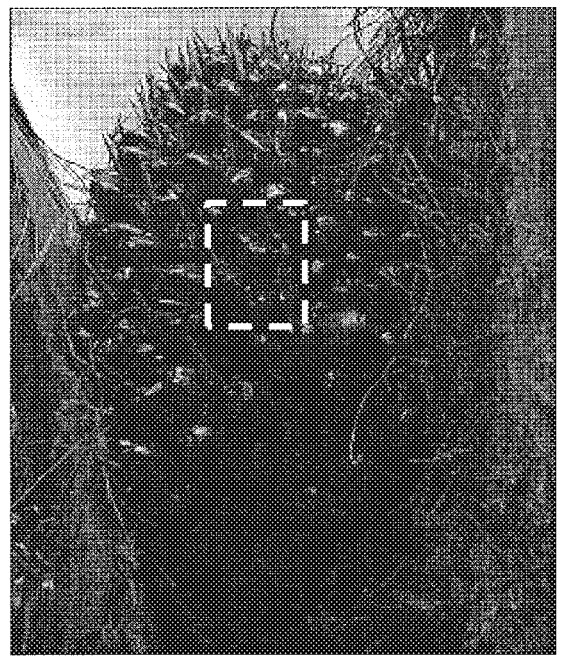
(b)
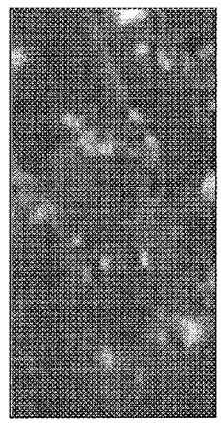
(c)
(d)

FIG.22C
(a)
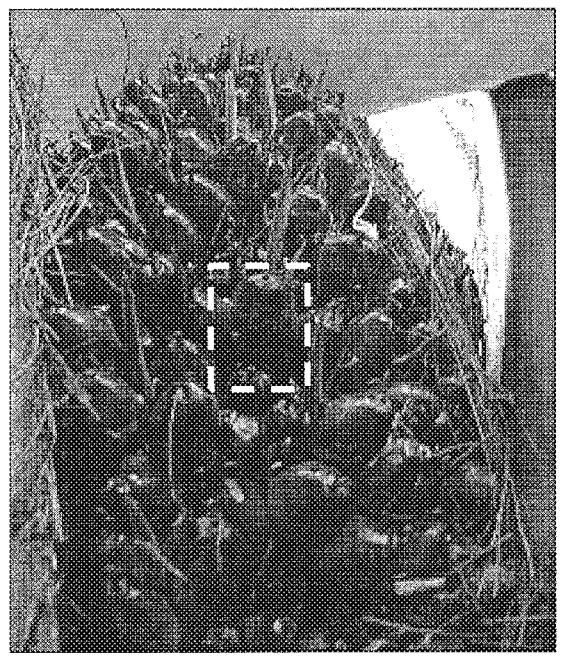
(b)　　　　　　(c)　　　　　　(d)
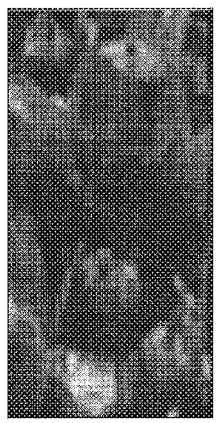  

FRUIT OR VEGETABLE PRODUCT HARVESTING APPARATUS AND FRUIT OR VEGETABLE PRODUCT HARVESTING METHOD

This application claims priority to Malaysian Patent Application No. PI 2016001488, filed on Aug. 10, 2016, the disclosure of which is hereby incorporated by reference in its entirety.

BACKGROUND OF THE INVENTION

1. Field of the Invention

The present invention relates to a fruit or vegetable product harvesting apparatus and a fruit or vegetable product harvesting method.

2. Description of the Related Art

The economic value of a harvesting target of fruits and vegetables depends on the content of a specific ingredient contained in the harvesting target. For example, an oil palm bunch (fresh fruit bunch) includes a large number of (e.g., 1,000 to 3,000) fruits, each of which includes pericarp (also referred to as "pulp"), mesocarp and a seed (also referred to as "palm kernel"). In the case where the harvesting target is an oil palm bunch, the content of oil in the mesocarp or palm kernel in a fruit is considered important. The oil contained in the mesocarp is generally called "palm oil", and the oil contained in the palm kernel is generally called "palm kernel oil". The content of oil in the oil palm fruit is known to be different in accordance with the maturity level of the oil palm bunch (specifically, fruits). Specifically, the oil content in a ripe fruit is known to be higher than the oil content in an unripe, underripe (slightly unripe) or overripe fruit. For example, the oil content in a fruit when being ripe is about three times the oil content therein when being unripe.

For example, in Malaysia, the Malaysian Palm Oil Board (MPOB) has established guidelines on the maturity level of fruits. Currently, harvesting workers working in oil palm plantations subjectively determine whether or not to harvest the fruits in accordance with the guidelines. As described above, the maturity level of the oil palm bunch significantly influences the yield of oil. Therefore, a wrong subjective determination of a harvesting worker (human error) on whether or not to harvest the fruits may have a significant influence on the yield. In actuality, it is difficult for a harvesting worker to correctly determine whether the fruits are ripe or underripe, which is a factor that decreases the yield of oil.

In such a situation, measurement devices have been developed for measuring various characteristics of an oil palm bunch, which is a subject (harvesting target), by use of near infrared light without destroying the oil palm bunch, namely, in a nondestructive manner. Such measurement devices irradiate the subject with near infrared light of a predetermined wavelength and measure a characteristic to be measured based on the reflectance of the light from the subject.

WO2012/074372 discloses a system that determines the maturity level of oil palm fruits using a hyperspectral imaging technology. WO2012/074372 also discloses the characteristic that the reflectance of the light of the near infrared wavelength band varies in accordance with the maturity level of the fruit. In this system, an image of a harvested oil palm bunch is captured by a spectral camera to acquire a sample image, and the sample image is analyzed based on the characteristic that the reflectance varies in accordance with the maturity level of the fruit to determine the maturity level of the oil palm fruit.

Japanese Laid-Open Patent Publication No. 2000-356591 discloses a nondestructive sugar content meter that calculates the sugar content of fruits and vegetables by a sugar content estimation equation by use of an output from a photoelectric conversion element based on light that has passed a near infrared light wavelength filter. Japanese Laid-Open Patent Publication No. Hei 8-122250 discloses a nondestructive measurement device that determines the maturity level of fruits and vegetables based on the intensity ratio between two specific wavelength components of near infrared light.

SUMMARY OF THE INVENTION

As described above, the economic value of a harvesting target depends on the content of a specific ingredient contained in the harvesting target. Therefore, it is desired to harvest the harvesting target at the time when the content of the specific ingredient in the harvesting target is high. For example, in the case where the harvesting target is an oil palm bunch, it is desired to harvest the oil palm bunch at the time when the content of the palm oil or palm kernel oil is high.

However, the system disclosed in WO2012/074372 is developed for indoor use, and outdoor use is not fully considered. Therefore, the system is of a large scale. In addition, the hyperspectral camera is costly, and thus the system is also costly. In a high-temperature, high-humidity environment, the hyperspectral camera is not considered durable. Therefore, it is very difficult to perform, for example, image capturing of an oil palm bunch in a tree in an oil palm plantation by use of the hyperspectral camera and determine the maturity level on the spot in order to determine an appropriate time to harvest the oil palm bunch. It is now assumed that the time to harvest is determined on the spot by use of the hyperspectral camera and an oil palm bunch having a high economic value is harvested. However, even in such a case, the load on the harvesting worker is increased by the large-scale system, which lowers the efficiency of the entire harvesting work. As a result, the producer does not fully enjoy the advantage that the economic value of the harvesting target is improved. The above-described human error does not allow the producer to fully enjoy the advantage.

The present invention made to solve the above-described problem provides a fruit or vegetable product harvesting apparatus and a fruit or vegetable product harvesting method capable of harvesting a harvesting target at the correct time to harvest without decreasing the efficiency of the harvesting work.

A harvesting apparatus for a fruit or vegetable product in an embodiment according to the present invention includes a maturity determination device which determines a maturity level of the fruit or vegetable product; a harvesting means harvesting the fruit or vegetable product; a power source which generates power for driving the harvesting means; and a controller determining whether or not to supply the power to the harvesting means based on a determination result on the maturity level provided by the maturity determination device.

In an embodiment, the maturity determination device may generate a control signal for turning on or off driving the harvesting means based on the determination result on the maturity level; and the controller may determine whether or not to supply the power to the harvesting means in accordance with the control signal.

In an embodiment, in the case where the maturity determination device determines that the maturity level has reached a predetermined level, the maturity determination device may generate a control signal for turning on the driving of the harvesting means, and the controller may determine to supply the power to the harvesting means; and in the case where the maturity determination device determines that the maturity level has not reached the predetermined level, the maturity determination device may generate a control signal for turning off the driving of the harvesting means, and the controller may determine not to supply the power to the harvesting means.

In an embodiment, the power source may start supplying the power in accordance with the determination made by the controller on the supply of the power.

In an embodiment, the harvesting apparatus may further include a switch circuit which performs switching, in accordance with the control signal, between a state of supplying the power from the power source to the harvesting means and a state of blocking the supply. The switch circuit may supply the power from the power source to the harvesting means in accordance with the determination made by the controller on the supply of the power.

In an embodiment, the harvesting apparatus may further include a notification device.

In an embodiment, the notification device may notify the maturity level based on the determination result on the maturity level.

In an embodiment, the maturity determination device may further determine whether the fruit or vegetable product is harvestable or not based on the determination result on the maturity level; and the notification device may notify whether the fruit or vegetable product is harvestable or not based on a determination result on whether the fruit or vegetable product is harvestable or not.

In an embodiment, in the case where the maturity determination device determines that the fruit or vegetable product is not harvestable, the notification device may notify that the fruit or vegetable product should not be harvested.

In an embodiment, the notification device may include at least one of an optical device emitting light based on the determination result on the maturity level, a sound output device outputting a sound based on the determination result on the maturity level, a vibration device vibrating based on the determination result on the maturity level, and a display device displaying maturity level information based on the determination result on the maturity level.

In an embodiment, the notification device may include at least one of an optical device emitting light based on the determination result on whether the fruit or vegetable product is harvestable or not, a sound output device outputting a sound based on the determination result on whether the fruit or vegetable product is harvestable or not, a vibration device vibrating based on the determination result on whether the fruit or vegetable product is harvestable or not, and a display device displaying information on whether the fruit or vegetable product is harvestable or not based on the determination result on whether the fruit or vegetable product is harvestable or not.

In an embodiment, the notification device may include a display device displaying a warning message based on the determination result on whether the fruit or vegetable product is harvestable or not; and in the case where the maturity determination device determines that the fruit or vegetable product is not harvestable, the display device may display the warning message that the fruit or vegetable product should not be harvested.

In an embodiment, the harvesting apparatus may further include an output interface which outputs maturity level determination information including the determination result on the maturity level.

In an embodiment, the harvesting apparatus may further include a printer which prints maturity level determination information including the determination result on the maturity level.

In an embodiment, the controller may generate use history information on a use history of the harvesting apparatus.

In an embodiment, the harvesting apparatus may further include an extendable rod-like support member. The harvesting means may be provided at a tip of the support member.

In an embodiment, the maturity determination device may include an image capturing module capturing an image of the fruit or vegetable product to generate image data; and the maturity determination device may determine the maturity level based on the image data.

In an embodiment, the image capturing module may include a plurality pixels arrayed one-dimensionally or two-dimensionally, and capture an image of at least a part of the fruit or vegetable product to acquire the image data; the plurality of pixels may include a plurality of first pixels each including a first light transmission filter selectively transmitting light of a first wavelength band, an intensity of light of the first wavelength band reflected by the fruit or vegetable product varying in accordance with the maturity level; and the maturity determination device may find an area size ratio of an intensity distribution of the light of the first wavelength band on the basis of a predetermined reference value based on a pixel value obtained from the plurality of first pixels, and determine the maturity level based on the area size ratio.

In an embodiment, the image capturing module may include a plurality pixels arrayed one-dimensionally or two-dimensionally, and capture an image of at least a part of the fruit or vegetable product to acquire the image data; the plurality of pixels may include a plurality of first pixels each including a first light transmission filter selectively transmitting light of a first wavelength band and a plurality of second pixels each including a second light transmission filter selectively transmitting light of a second wavelength band, an intensity of light of the first wavelength band reflected by the fruit or vegetable product varying in accordance with the maturity level, and an intensity of light of the second wavelength band reflected by the fruit or vegetable product being generally constant regardless of the maturity level; and the maturity determination device may find an area size ratio of an intensity distribution of the light of the first wavelength band on the basis of a predetermined reference value based on pixel values obtained from the plurality of first pixels and the plurality of second pixels, and determine the maturity level based on the area size ratio.

In an embodiment, the fruit or vegetable product may be a bunch with a large number of fruits.

In an embodiment, the maturity determination device may include an image capturing module capturing an image of the fruit or vegetable product to generate image data; and the image capturing module may be provided in the vicinity of the tip of the support member.

A method in an embodiment according to the present invention is a method for harvesting a fruit or vegetable product using a harvesting apparatus including a maturity determination device which determines a maturity level of the fruit or vegetable product and a harvesting means harvesting the fruit or vegetable product. The method includes the steps of determining the maturity level of the fruit or vegetable product by the maturity determination device to acquire a determination result on the maturity level; making a determination on an operation of the harvesting means based on the determination result on the maturity level; and harvesting the fruit or vegetable product based on the determination on the operation of the harvesting means.

In an embodiment, in the case where the determination result on the maturity level indicates that the maturity level has reached a predetermined level in the step of acquiring the determination result on the maturity level, a determination may be made to permit the harvesting means to be operated in the step of making a determination on the operation of the harvesting means; and in the case where the determination result on the maturity level indicates that the maturity level has not reached the predetermined level in the step of acquiring the determination result on the maturity level, a determination may be made not to permit the harvesting means to be operated in the step of making a determination on the operation of the harvesting means.

In an embodiment, the method may further include the step of notifying the maturity level based on the determination result on the maturity level.

In an embodiment, in the step of acquiring the determination result on the maturity level, it may be determined whether the fruit or vegetable product is harvestable or not based on the determination result on the maturity level to acquire a determination result on whether the fruit or vegetable product is harvestable or not; and the method ma further include the step of notifying whether the fruit or vegetable product is harvestable or not based on the determination result on whether the fruit or vegetable product is harvestable or not.

In an embodiment, the method may further include the step of, in the case where the fruit or vegetable product is determined as not being harvestable in the step of acquiring the determination result on the maturity level, warning a user of the harvesting apparatus that the fruit or vegetable product should not be harvested.

In an embodiment, in the step of making a determination on the operation of the harvesting means, a determination may be made not to permit the harvesting means to be operated, as well as said warning the user of the harvesting apparatus that the fruit or vegetable product should not be harvested.

In an embodiment, the method may further include the step of outputting maturity level determination information including the determination result on the maturity level.

In an embodiment, the method may further include the step of printing maturity level determination information including the determination result on the maturity level.

In an embodiment, the method may further include the step of generating use history information representing a use history of the harvesting apparatus.

In an embodiment, the step of acquiring the determination result on the maturity level may include the steps of receiving an image including at least a part of the fruit or vegetable product, the image including at least an intensity distribution of light of a first wavelength band, an intensity of the light of the first wavelength band reflected by the fruit or vegetable product varying in accordance with the maturity level; finding an area size ratio of the intensity distribution of the light of the first wavelength band on the basis of a predetermined reference value; and determining the maturity level in accordance with the area size ratio to acquire the determination result on the maturity level.

In an embodiment, the step of acquiring the determination result on the maturity level may include the steps of receiving an image including at least a part of the fruit or vegetable product, the image including at least an intensity distribution of light of a first wavelength band and an intensity distribution of light of a second wavelength band, an intensity of the light of the first wavelength band reflected by the fruit or vegetable product varying in accordance with the maturity level, and an intensity of the light of the second wavelength band reflected by the fruit or vegetable product being generally constant regardless of the maturity level; finding an area size ratio of the intensity distribution of the light of the first wavelength band on the basis of a predetermined reference value and in consideration of the intensity distribution of the light of the second wavelength band; and determining the maturity level in accordance with the area size ratio to acquire the determination result on the maturity level.

In an embodiment, the step of acquiring the determination result on the maturity level may further include the step of capturing an image of at least a part of the fruit or vegetable product to acquire the image data.

In an embodiment, the fruit or vegetable product may be a bunch with a large number of fruits.

A computer program in an embodiment according to the present invention is to be executed by a computer usable for a harvesting apparatus including a maturity determination device which determines a maturity level of the fruit or vegetable product and a harvesting means harvesting the fruit or vegetable product. The computer program cause the computer to execute the steps of determining the maturity level of the fruit or vegetable product by the maturity determination device to acquire a determination result on the maturity level; making a determination on an operation of the harvesting means based on the determination result on the maturity level; and harvesting the fruit or vegetable product based on the determination on the operation of the harvesting means.

According to an embodiment of the present invention, a fruit or vegetable product harvesting apparatus and a fruit or vegetable product harvesting method capable of harvesting a harvesting target at the correct time to harvest without decreasing the efficiency of the harvesting work are provided.

BRIEF DESCRIPTION OF THE DRAWINGS

FIG. 12 shows images I acquired by image capturing of the entirety of the bunch F of each of three maturity levels, and pixel distributions, at the respective maturity levels, of pixels having a pixel value larger than, or equal to, a reference value among the pixels that have a pixel value NIRS and are included in the images I.

FIG. 13A shows an image I of the unripe bunch F and a mapping image obtained as a result of mapping performed based on the pixel value NIRS of a plurality of first pixels in the image I.

FIG. 13B shows an image I of the underripe bunch F and a mapping image obtained as a result of mapping performed based on the pixel value NIRS of a plurality of first pixels in the image I.

FIG. 13C shows an image I of the ripe bunch F and a mapping image obtained as a result of mapping performed based on the pixel value NIRS of a plurality of first pixels in the image I.

FIG. 21 is a flowchart showing a procedure by which the maturity determination device 100 of the harvesting apparatus 1000A in embodiment 2 generates maturity level determination information in detail.

FIG. 22A shows an image I of the unripe bunch F and a mapping image obtained as a result of mapping performed based on the pixel value NIRS of a plurality of first pixels in the image I.

FIG. 22B shows an image I of the underripe bunch F and a mapping image obtained as a result of mapping performed based on the pixel value NIRS of a plurality of first pixels in the image I.

FIG. 22C shows an image I of the ripe bunch F and a mapping image obtained as a result of mapping performed based on the pixel value NIRS of a plurality of first pixels in the image I.

DETAILED DESCRIPTION OF PREFERRED EMBODIMENTS

Figure 1:
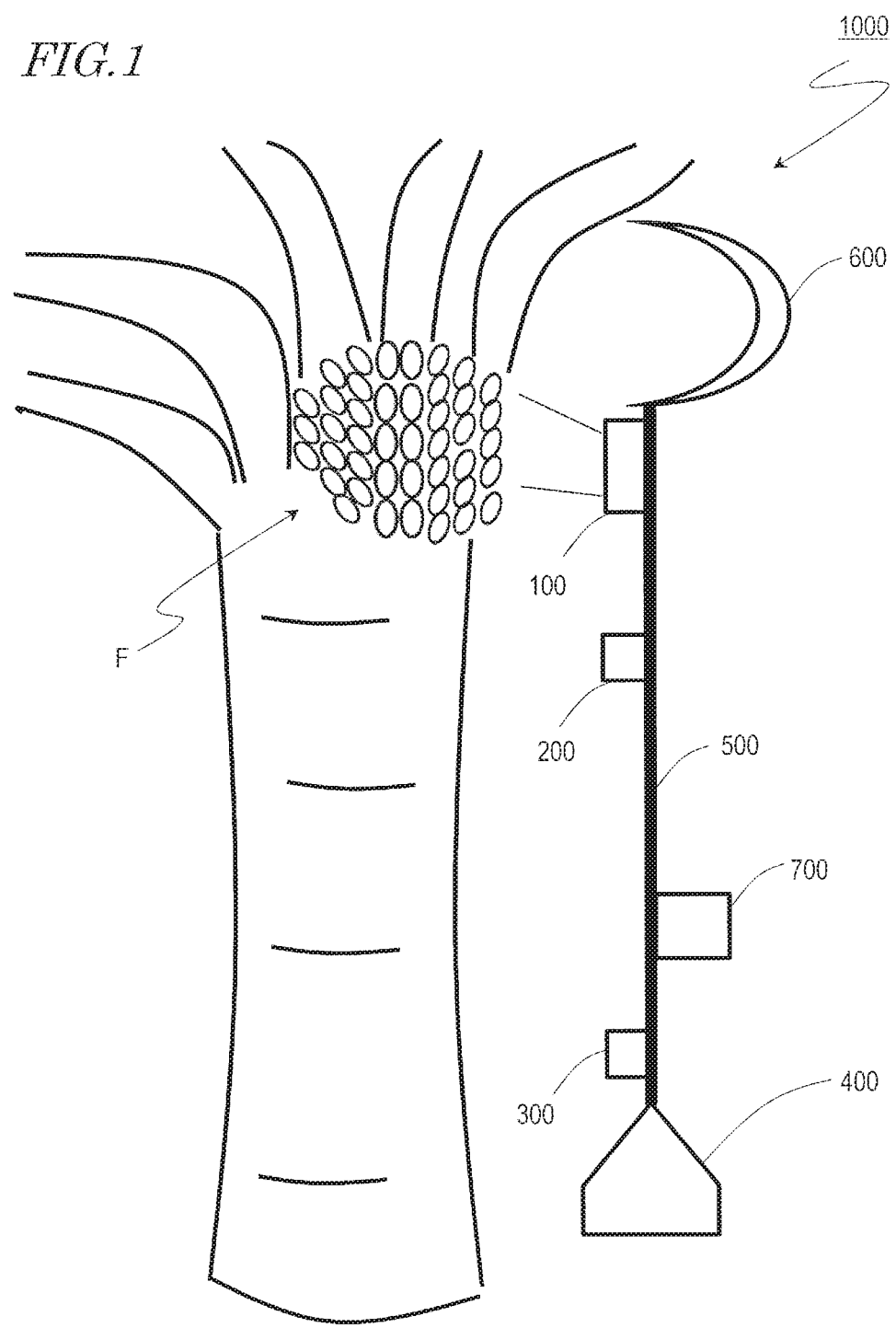
FIG. 1 schematically shows an entire structure of a harvesting apparatus 1000 in embodiment 1.

A harvesting apparatus for a fruit or vegetable product in an embodiment according to the present invention (hereinafter, referred to as the "harvesting apparatus") includes a maturity determination device determining a maturity level of the fruit or vegetable product; a harvesting means harvesting the fruit or vegetable product; a power source generating power for driving the harvesting means; and a controller determining whether or not to supply the power to the harvesting means based on a determination result on the maturity level provided by the maturity determination device. This harvesting apparatus is preferably usable as a harvesting apparatus harvesting an oil palm bunch including a larger number of fruits. With this harvesting apparatus, the maturity level of the oil palm bunch may be determined without significantly increasing the time or work for the determination on the maturity level. In addition, the oil palm bunch may be automatically reaped in accordance with the determination result on the maturity level.

A method for harvesting a fruit or vegetable product in an embodiment according to the present invention (hereinafter, referred to as a "harvesting method") is a harvesting method using a harvesting apparatus including a maturity determination device determining a maturity level of the fruit or vegetable product and a harvesting means harvesting the fruit or vegetable product. The harvesting method includes the steps of determining the maturity level of the fruit or vegetable product by the maturity determination device to acquire a determination result on the maturity level; making a determination on an operation of the harvesting means based on the determination result on the maturity level; and harvesting the fruit or vegetable product based on the determination on the operation of the harvesting means. This harvesting method is preferably usable for a harvesting apparatus harvesting an oil palm bunch including a larger number of fruits. With this harvesting method, the oil palm bunch is suppressed from being harvested by an error at the timing not to harvest the oil palm bunch.

In this specification, a harvesting apparatus and a harvesting method for an oil palm bunch, which is an example of fruit or vegetable product. In this specification, any type or any part of fruit or vegetable that is to be harvested is referred to as a "fruit or vegetable product". As described below, the present invention encompasses determining the maturity level of a fruit or vegetable product with which the reflectance of light in a specific wavelength band varies in accordance with the maturity level, for example, coffee fruits, apples and mangoes, and harvesting such a fruit or vegetable product in accordance with the determination.

Hereinafter, a harvesting apparatus and a harvesting method in embodiments according to the present invention will be described with reference to the attached drawings. In the following description, identical or similar elements will bear the identical reference signs to each other. The harvesting apparatus and the harvesting method in an embodiment according to the present invention are not limited to those in any of the following embodiments. For example, one embodiment and another embodiment may be combined together.

(Embodiment 1)

With reference to FIG. 1 through FIG. 19, a structure of a harvesting apparatus in this embodiment and an operation thereof (harvesting method for which the harvesting apparatus is usable) also in this embodiment will be described.

[Structure of the Harvesting Apparatus 1000]

Figure 2:
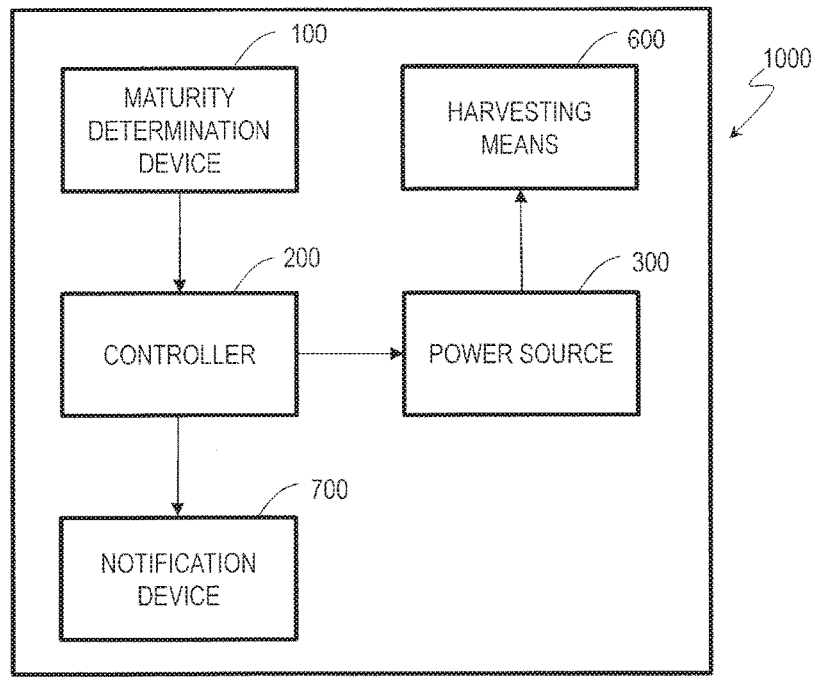
FIG. 2 is a block diagram schematically showing an example of hardware structure of the harvesting apparatus 1000.

FIG. 1 schematically shows an entire structure of the harvesting apparatus 1000. FIG. 2 schematically shows an example of hardware structure of the harvesting apparatus 1000. The harvesting apparatus usable to harvest an oil palm bunch may be called a "palm cutter".

The harvesting apparatus 1000 typically includes a maturity determination device 100, a controller 200, a power source 300, a handle 400, a support member 500, a harvesting means 600, and a notification device 700. As described below, the notification device 700 is an optional element. The harvesting apparatus 1000 in this embodiment is capable of automatically performing a series of operations including determination of the maturity level of an oil palm bunch F, determination on supply of the power based on the determination result, reaping of the oil palm bunch F by the harvesting means 600 and the like.

The maturity determination device 100 captures an image of the oil palm bunch F (hereinafter, referred to as the "bunch F") and analyzes the captured image to determine the maturity level. The "maturity level" is the degree of ripening of the bunch F, and may be classified into, for example, "ripe", "underripe" and "unripe". Needless to say, the maturity level may be classified into a larger number of levels. For example, the level "overripe" may be provided. A level representing another maturity level (e.g., "slightly ripe" may be provided between "ripe" and "underripe". The structure and the function of the maturity determination device 100 will be described below in detail.

The controller 200 is a semiconductor integrated circuit (LSI) and may be realized by, for example, a microcontrol unit (MCU). The controller 200 is electrically connected with each of, for example, the maturity determination device 100, the power source 300, and the notification device 700, and controls the entirety of the harvesting apparatus 1000. For example, the controller 200 determines whether or not to supply power generated by the power source 300 to the harvesting means 600 based on the determination result on the maturity level provided by the maturity determination device 100. The controller 200 may generate a driving signal for driving the notification device 700 based on the determination result on the maturity level.

The power source 300 may be, for example, a gasoline engine, a diesel fuel engine, a set of an electric motor and a battery, or a set of an electric motor and a solar cell. The power source 300 generates power for driving the harvesting means 600. For example, the electric energy accumulated in the battery is converted into a mechanical energy by the electric motor, and the mechanical energy is transmitted as the power to the harvesting means 600 via a gear (not shown). The power source 300 may, for example, include an MCU (not shown) usable to communicate with the controller 200.

The handle 400 is a member by which an operator (harvesting worker) holds the harvesting apparatus 1000, and is provided at, for example, one end (tip) of the support member 500.

The support member 500 is a rod-like member. Preferably, the support member 500 is an extendable rod-like member. With such an arrangement, the length of the harvesting apparatus 1000 is adjustable in accordance with the distance (height) to the bunch F of the harvesting target.

The harvesting means 600 is configured to reap the base, frond and limb of the bunch F, and has a shape of, for example, a sickle or a chisel. The harvesting means 600 is operable automatically by the power, not manually, to reap the bunch F or the like. The harvesting means 600 may be realized by, for example, an engine chainsaw, an electric saw, electric scissors, or an electric cutter. For example, the harvesting means 600 is provided at the other end of the support member 500, namely, on the opposite end to the handle 400. The maturity determination device 100 may be located in the vicinity of the tip of the harvesting apparatus 1000. Preferably, the maturity determination device 100 is located in the vicinity of the harvesting means 600. With such a positional arrangement, the determination on the maturity level of the bunch F and the work of harvesting the bunch F are performed concurrently. Therefore, an efficient operation is realized.

The maturity determination device 100 may be detachable from the harvesting apparatus 1000. In this case, the harvesting apparatus 1000 may further include an attachment unit that is separate from the support member 500 and allows the maturity determination device 100 to be attached thereto.

The notification device 700 notifies the worker of the maturity level of the bunch F or of whether the bunch F is harvestable or not based on the determination result on the maturity level provided by the maturity determination device 100. The notification device 700 includes at least one of an optical device emitting light based on the determination result on the maturity level, a sound output device outputting a sound based on the determination result on the maturity level, a vibration device vibrating based on the determination result on the maturity level, and a display device displaying maturity level information based on the determination result on the maturity level. The optical device is, for example, an LED (Light Emitting Diode) lamp. The sound output device is, for example, a speaker. The vibration device is, for example, a vibrator. The display device is, for example, a liquid crystal display or an organic EL (Electroluminescence) display.

Figure 3:
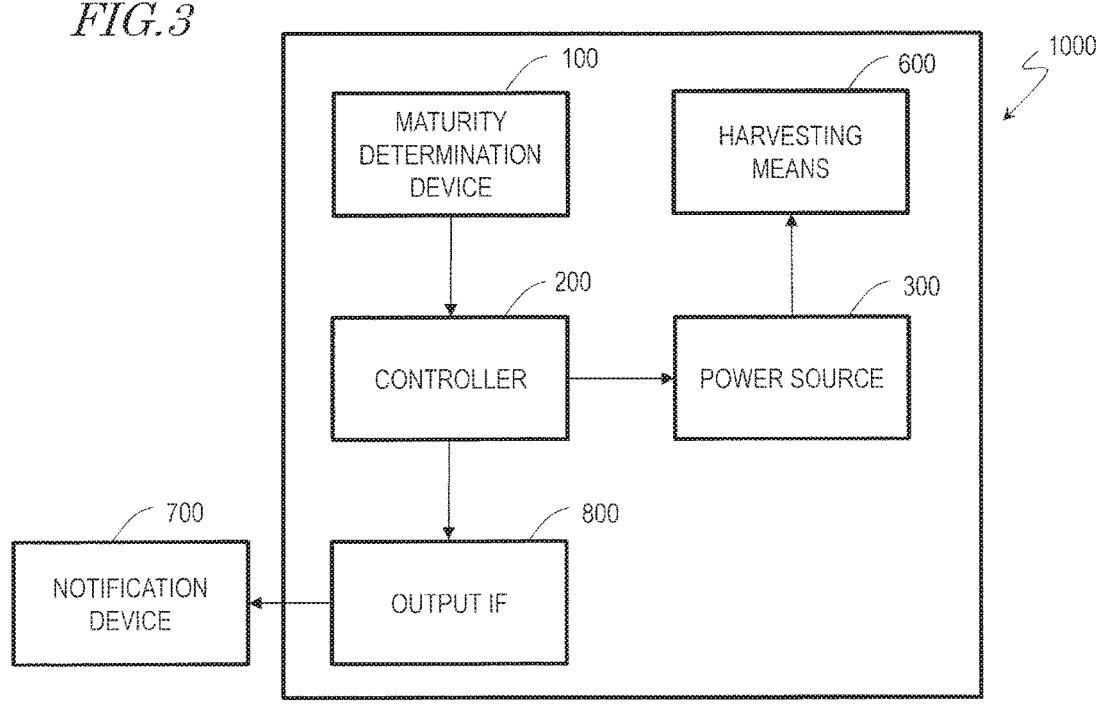
FIG. 3 is a block diagram schematically showing another example of hardware structure of the harvesting apparatus 1000.

FIG. 3 schematically shows another example of hardware structure of the harvesting apparatus 1000. As shown in FIG. 3, the notification device 700 may be an external device externally attachable to the harvesting apparatus 1000. The harvesting apparatus 1000 includes an output IF 800 outputting image capturing data, data representing maturity level information or the like to an external device. The harvesting apparatus 1000 is connected with the notification device 700 in a wired or wireless manner via the output IF 800. In the case of wireless connection, the output IF 800 may be a communication interface conformed to, for example, the Bluetooth (registered trademark) standards or the Wi-Fi (registered trademark) standards. In the case of wired connection, the output IF 800 may be a communication interface conformed to, for example, the USB or HDMI (registered trademark) standards. The notification device 700, when being used as an external device, may be a portable device such as, for example, a smartphone, a tablet, a laptop computer or the like.

Data transmission and receiving between the blocks (elements) shown in FIG. 2 or FIG. 3 may be performed by wired or wireless communication. For example, the blocks may be connected with each other by use of a wire harness. The wire harness may be, for example, installed inside the support member 500, or exposed outside. Alternatively, the blocks may be connected with each other by wireless communication conformed to the Bluetooth or Wi-Fi standards described above. In this case, for example, the maturity determination device 100, the controller 200, the power source 300 and the notification device 700 each include a wireless communication module. Naturally, the blocks may be connected with each other by a combination of wired communication and wireless communication.

Figure 4:
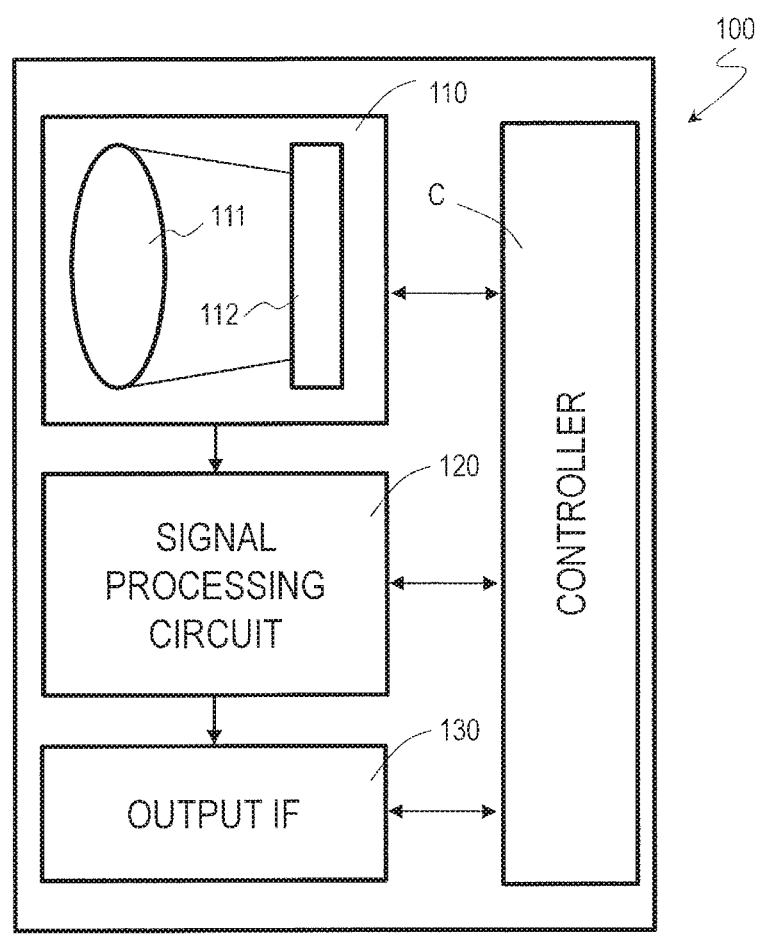
FIG. 4 is a block diagram schematically showing an example of hardware structure of a maturity determination device 100.

FIG. 4 schematically shows an example of hardware structure of the maturity determination device 100.

The maturity determination device 100 includes an image capturing module 110, a signal processing circuit 120, an output IF 130, and a controller C. The image capturing module 110 of the maturity determination device 100 performs image capturing of at least a part of a large number of fruits in the bunch F to acquire an image of the fruits. In this case, it is preferable that the image includes at least three fruits. The signal processing circuit 120 analyzes the image to generate maturity level determination information representing the maturity level of the bunch F. The generated maturity level determination information is, for example, output outside via the output IF 130.

The image capturing module 110 includes a lens 111 and an image sensor 112.

The lens (or lens group) 111 collects light from the bunch F onto an image capturing surface of the image sensor 112. The lens 111 may be a single lens or include a plurality of lenses. The lens 111 may include a lens for autofocus (AF) and/or a lens for optical zooming. The lens for AF and the lens for optical zooming are drivable by a dedicated driver (not shown). The image capturing module 110 may include a control circuit (not shown) controlling such a driver.

The image sensor 112 is, for example, a CCD (Charge Coupled Device) sensor or a CMOS (Complementary Metal Oxide Semiconductor) sensor. The image sensor 112 includes a plurality of pixels arrayed one-dimensionally or two-dimensionally (pixel array). In the case where the plurality of pixels are arrayed one-dimensionally, the image sensor 112 may be a line sensor.

Figure 5:
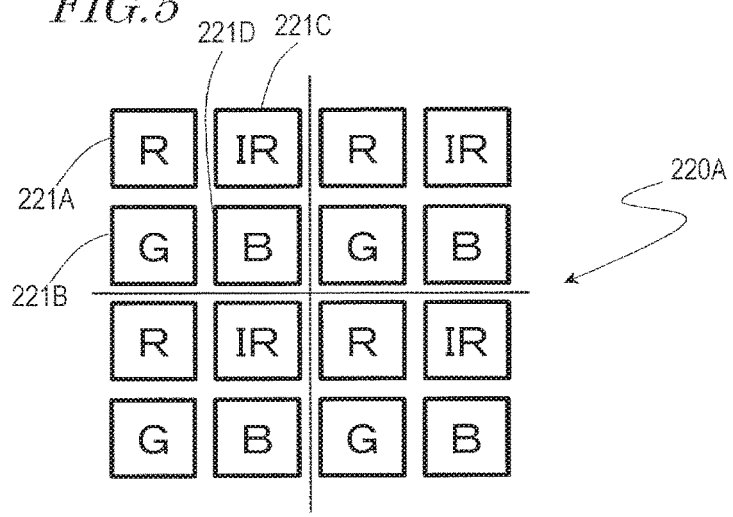
FIG. 5 shows pixels arrayed in four rows by four columns among a plurality of pixels 221 arrayed two-dimensionally in a pixel array 220A.
Figure 6:
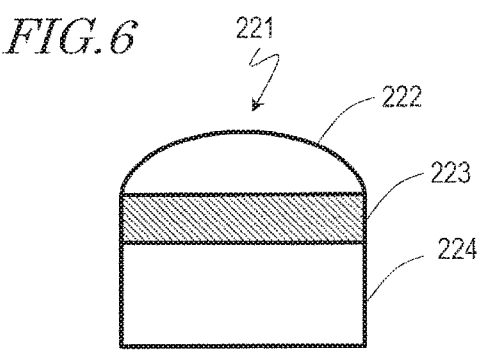
FIG. 6 schematically shows a cross-section of the pixel 221 that is parallel to an optical axis of a microlens 222.
Figure 7:
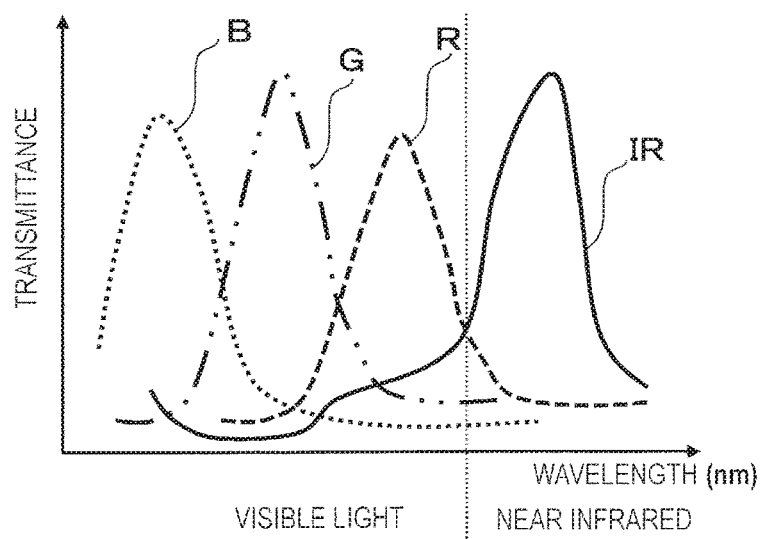
FIG. 7 is a graph showing the light transmittance characteristic of a light transmission filter 223.

FIG. 5 shows a part of a plurality of pixels 221 arrayed two-dimensionally in a pixel array 220A, more specifically, the pixels 221 arrayed in four rows by four columns. FIG. 6 schematically shows a cross-section of the pixel 221 that is parallel to an optical axis of a microlens 222. FIG. 7 shows a light transmittance characteristic of a light transmission filter 223. In the graph of FIG. 7, the horizontal axis represents the wavelength (nm) of the light, and the vertical axis represents the transmittance of the light transmission filter 223.

The image sensor 112 includes the plurality of pixels 221 arrayed two-dimensionally (pixel array 220A). The pixels 221 each include the microlens 222, the light transmission filter 223 and a photoelectric conversion element 224.

The microlens 222 is located on the light transmission filter 223, and collects light from the bunch F to improve the pixel sensitivity. The light transmission filter 223 selectively transmits light of a specific wavelength band. For example, the light transmission filter 223 is either an IR filter or one of RGB color filters. As shown in FIG. 7, the IR filter selectively transmits light of a near infrared wavelength band (e.g., 800 nm to 2500 nm), and preferably selectively transmits light of a wavelength band of 800 nm to 900 nm. An R filter selectively transmits light of a red wavelength band (e.g., 620 nm to 750 nm). A G filter selectively transmits light of a green wavelength band (e.g., 500 nm to 570 nm). A blue filter selectively transmits light of a blue wavelength band (e.g., 450 nm to 500 nm).

The photoelectric conversion element 224 is typically a photodiode (PD), and converts received light into an electric signal. The PD is, for example, embedded in a semiconductor substrate formed of silicon (not shown).

As shown in FIG. 5, the pixel array 220A has pixel units each including pixels 221A, 221B, 221C and 221D arrayed in two rows by two columns. The pixels 221A, 221B, 221C and 221D respectively include an R filter, a G filter, an IR filter and a B filter. Such an array corresponds to an array obtained as a result of a G filter in an odd or even number column of a Bayer array being replaced with an IR filter. In this specification, the pixels 221A, 221B, 221C and 221D included in one pixel unit are associated with each other. As described below, pixel values of the pixels associated with each other (e.g., pixels 221C and 221D) may be subjected to division.

Any of various pixel unit patterns other than the above-described pixel unit pattern may be selected. For example, the pixel unit does not need to include the G filter among the four filters, or may include only the IR filter and the R filter. The number of each type of filters included in the pixel unit is arbitrary. The pixel unit is not limited to include 2×2 pixels, and may include 4×4 pixels. With the maturity level determination in this embodiment, the pixel value obtained from the pixel 221C including the IR filter is considered important.

In this specification, the "pixel value" is, for example, an 8-bit gray scale value, and mainly refers to RAW data. In this specification, the pixel value may be referred to as the "gray scale value". The image capturing module 110 at least outputs RAW data. Alternatively, the image capturing module 110 may have a function of generating a luminance/color difference signal based on the RAW data and outputting the luminance/color difference signal.

As described below in detail, the reflectance of light (intensity of reflected light) of a first wavelength band from, for example, the bunch F varies in accordance with the maturity level. The first wavelength band is, for example, a near infrared wavelength band. In the case where the maturity level of a fruit or vegetable product exhibiting such a characteristic is to be found, the unit pixel merely needs to include at least the IR filter. For example, the four filters in the pixel unit shown in FIG. 5 may all be the IR filters. Even in such a case, the maturity level determination in this embodiment may be performed. However, it is preferable that the unit pixel includes the RGB filters from the point of view of generating a color image.

Now, FIG. 4 will be referred to again.

The controller C is an LSI, and may be for example, a general-purpose processor. The controller C is electrically connected with each of the image capturing module 110, the signal processing circuit 120 and the output IF 130, and controls the entirety of the maturity determination device 100.

Figure 8:
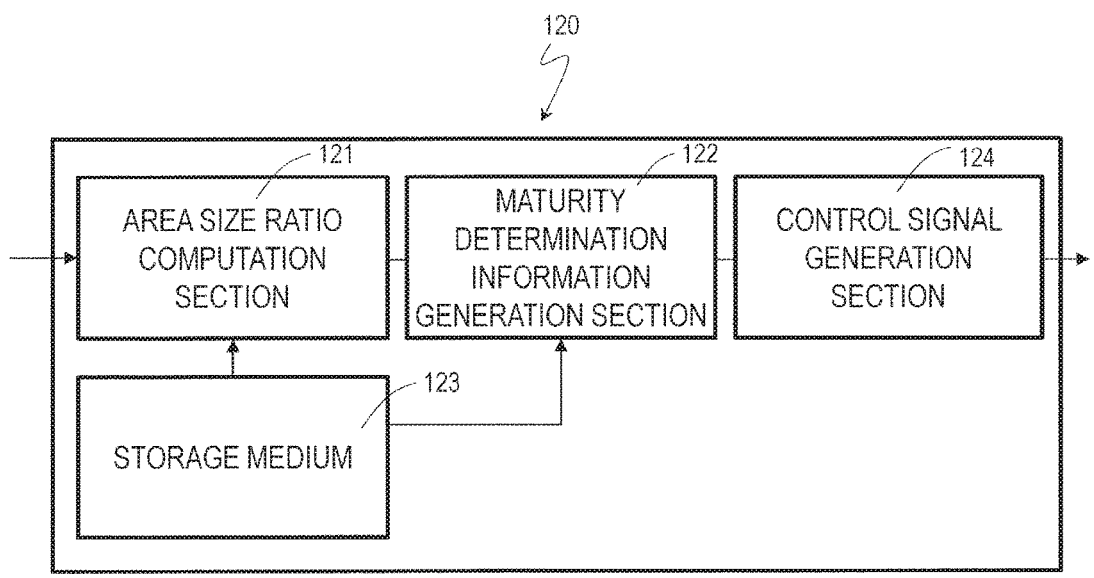
FIG. 8 is a functional block diagram schematically showing functional blocks of a signal processing circuit 120.

FIG. 8 schematically shows functional blocks of the signal processing circuit 120. Elements of the signal processing circuit 120 are shown in functional block units, instead of hardware units.

The signal processing circuit 120 is an LSI, and is, for example, an image signal processor (ISP). The signal processing circuit 120 analyzes image data that is output from the image capturing module 110 to generate maturity level determination information on the bunch F. The signal processing circuit 120 includes an area size ratio computation section 121, a maturity level determination information generation section 122, a storage medium 123, a control signal generation section 124, and a computation core (not shown). For example, the storage medium 123 is a read-only or writable ROM, RAM or hard disc. Each block of the area size ratio computation section 121, the maturity level determination information generation section 122, and the control signal generation section 124 are realized by either hardware or software. In the case where being realized by software, each block may be a computer program including a group of commands for realizing the corresponding function. Such a computer program is stored on, for example, the storage medium 123. For example, the computer program stored on the storage medium 123 is once loaded onto the RAM (not shown) and executed by the computation core.

The signal processing circuit 120 may have a function of performing a process commonly performed for image processing, for example, gamma correction, color interpolation, spatial interpolation, and auto-white balance. The signal processing circuit 120 may generate a color image based on the pixel values obtained from the RGB pixels including RGB filters.

Now, FIG. 4 will be referred to again.

The output IF 130 is an interface outputting the maturity level determination information generated by the signal processing circuit 120 to the controller 200 external to the maturity determination device 100. For example, the output IF 130 may be a communication interface conformed to the Bluetooth standards or the Wi-Fi standards, or a communication interface conformed to the USB or HDMI standards, like the output IF 800.

[Operation of the Harvesting Apparatus 1000]

Figure 9:
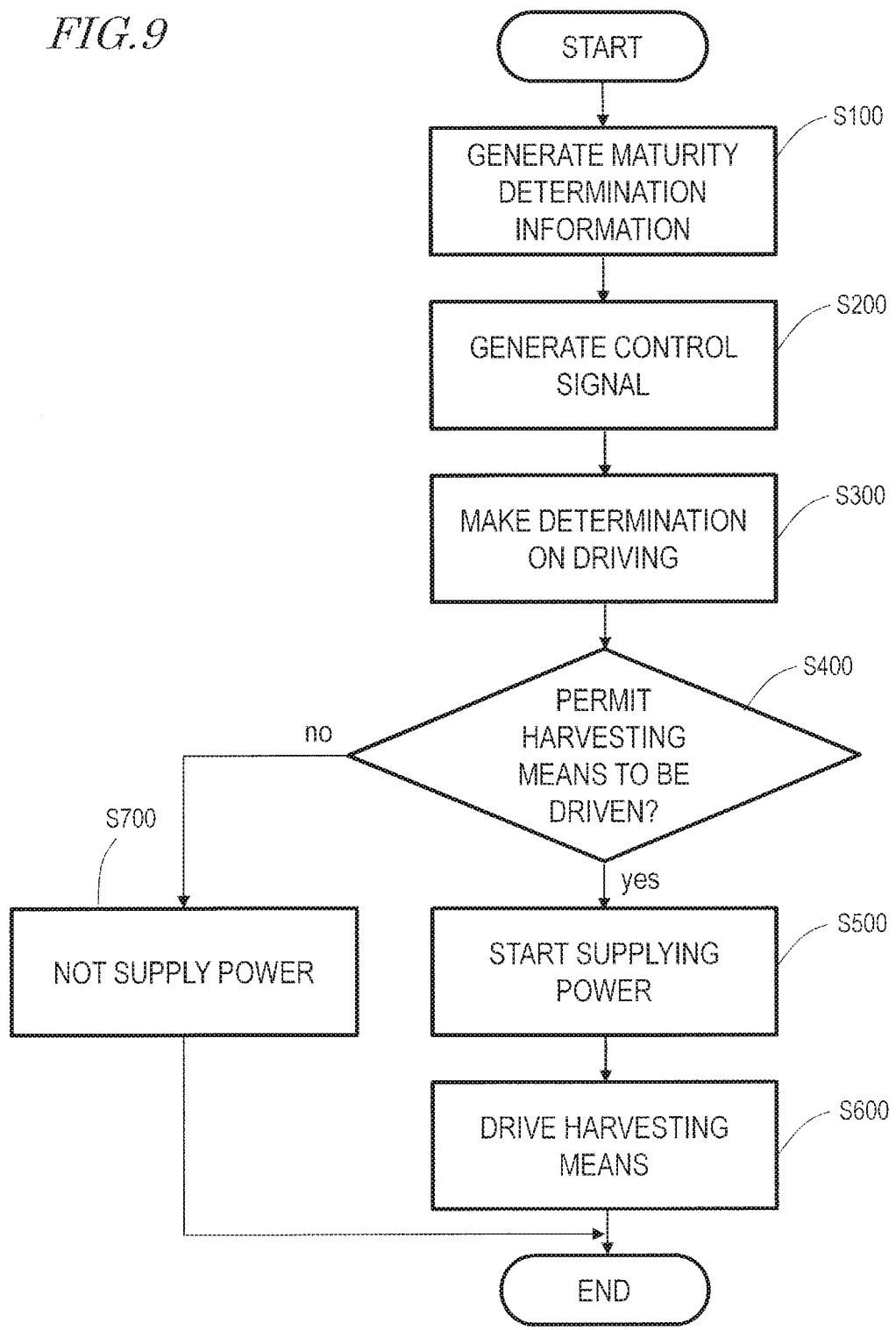
FIG. 9 is a flowchart showing an example of operation procedure of the harvesting apparatus 1000 in embodiment 1.

FIG. 9 shows an example of operation procedure of the harvesting apparatus 1000 in this embodiment.

The harvesting apparatus 1000 is operable in accordance with the operation procedure shown in FIG. 9. The operation procedure corresponds to a harvesting method for which the harvesting apparatus 1000 is usable.

First, the image capturing module 110 of the maturity determination device 100 performs image capturing of the bunch F to acquire an image of the bunch F, and analyzes the image to generate maturity level determination information representing the maturity level of the bunch F (step S100).

Figure 10:
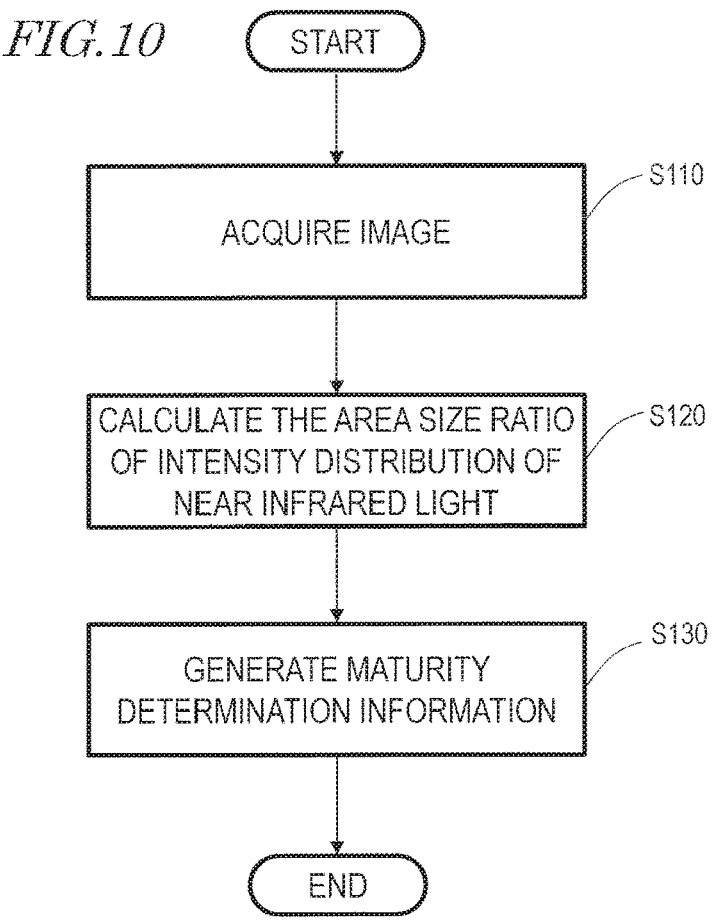
FIG. 10 is a flowchart showing a procedure by which the maturity determination device 100 generates maturity level determination information in detail.

FIG. 10 shows a procedure by which the maturity determination device 100 generates the maturity level determination information in detail.

The image capturing module 110 performs image capturing of all of, or a part of, the large number of fruits in the bunch F (preferably, at least three fruits) to acquire an image I (step S110). As described below, the image capturing module 110 may perform image capturing of the entirety of the oil palm tree. The image capturing module 110 may acquire the image I by performing image capturing of a central part and the vicinity thereof of the bunch F. Moreover, the image capturing device 200 preferably acquires the image I through image capturing of a well-sunlit portion of the bunch F, e.g., a tip thereof. The reason is that, presumably, the fruits in a sunlit portion of the bunch F will be the first to start maturing. The image capturing module 110 may perform the image capturing a plurality of times to acquire the image I a plurality of times. The acquired pieces of image data may be added together to improve the SN ratio. The acquired image I includes an intensity distribution of at least near infrared light reflected by the bunch F. In this embodiment, the image I includes intensity distributions of the near infrared light, red light, green light and blue light reflected by the bunch F. In other words, the image I includes pixel values (image data) REDS, GLNS, NIRS and BLUS respectively obtained from the four pixels 221A, 221B, 221C and 221D. In an embodiment of the present invention, the image I merely needs to include an intensity distribution of at least the near infrared light.

Figure 11:
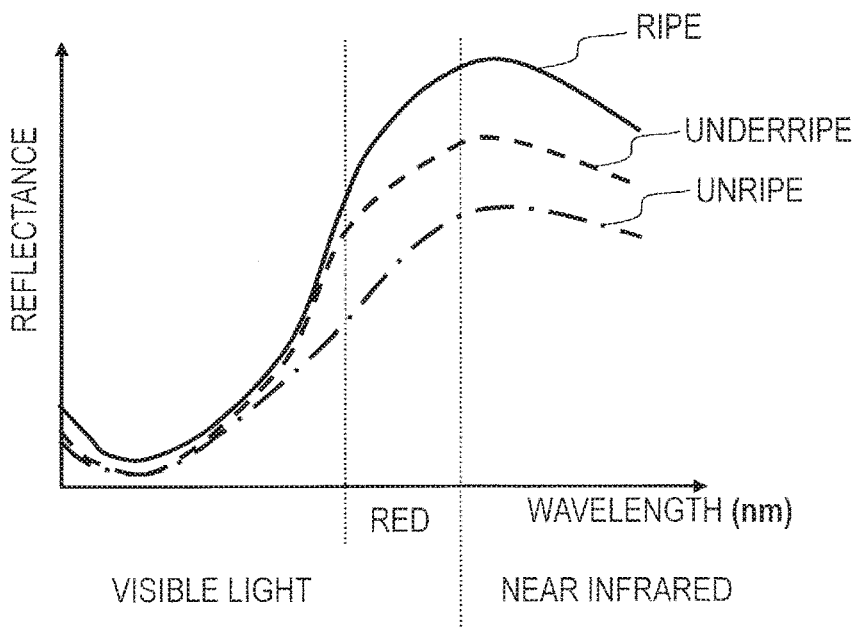
FIG. 11 is a graph schematically showing how the intensity of the reflected light (reflectance) varies in accordance with the maturity level at the time of harvest of a bunch F.

FIG. 11 schematically shows how the intensity of the reflected light (reflectance) varies in accordance with the maturity level at the time of harvest of the bunch F. The horizontal axis represents the wavelength of the light (nm), and the vertical axis represents the reflectance. In general, the image sensor 112 (e.g., image sensor using silicon) has a sensitivity characteristic depending on the wavelength of the light. Generally, for measuring the reflectance in consideration of the sensitivity characteristic, the pixel value that is output from the image sensor 112 is standardized by use of a standard white plate. The standard white plate is a highly reflective diffuse reflection plate that generates diffuse reflection light not depending on the angle. The reflectance represented by the vertical axis of FIG. 11 shows the ratio of the reflectance of light reflected by the bunch F with respect to the reflectance measured by use of the standard white plate.

The maturity level may be classified into, for example, three levels of "ripe", "underripe" and "unripe". At the time of harvest of the oil palm bunch F, the light reflected by the bunch F has a reflectance characteristic that the intensity increases as the light has a longer wavelength within the wavelength band from the blue light to the near infrared light. Especially in a wavelength band of the red light, which is visible light, the reflectance characteristic is exhibited that the intensity increases as the maturity level of the bunch F rises. Also in the near infrared light wavelength band having the maximum wavelength of the reflected light that may be received in accordance with the sensitivity characteristic of the image sensor 112, the reflectance characteristic is exhibited that the intensity increases as the maturity level of the bunch F rises. As can be seen, especially in the wavelength band from the red light to the near infrared light, the reflectance is represented by a curve unique to the maturity level. As described below in detail, an appropriate threshold value for the reflectance may be set in each wavelength band based on the curve and the reflectance and the threshold value may be compared against each other, so that the maturity level is determined.

In this embodiment according to the present invention, the image I including the intensity distribution of at least the near infrared light may be analyzed, so that the maturity level is determined. In this embodiment, the maturity level is determined based on the pixel value NIRS. Therefore, for example, the pixel unit including the pixels 221 in two rows by two columns shown FIG. 5 preferably includes the pixels 221C including the IR filter in the largest number.

The signal processing circuit 120, specifically, the area size ratio computation section 121 (see FIG. 8) of the signal processing circuit 120, calculates an area size ratio of the intensity distribution of the near infrared light in the acquired image I. The image I includes a plurality of first pixels (or image data) including information representing the intensity distribution of the near infrared light, a plurality of second pixels including information representing an intensity distribution of the blue light, a plurality of third pixels including information representing an intensity distribution of the green light, and a plurality of fourth pixels including information representing an intensity distribution of the red light. As described above, the image I merely needs to include at least the plurality of first pixels.

FIG. 12 shows the images I acquired by image capturing of the entirety of the bunches F respectively of three maturity levels (unripe, underripe and ripe), and also shows, for each maturity level, the distribution of the pixels having a pixel value higher than, or equal to, a reference value, among the pixels having the pixel value NIRS included in the pixel I. In this embodiment, the pixel value is represented by, for example, the 8-bit system (values of 0 to 255). The reference value may be, for example, "80".

It is now assumed that all the pixel values in the image I including the entirety of the bunch F are simply averaged. The average value may vary by an influence of the background, the shadow between the fruits or the like, which may be included in the image I. With the maturity level determination in this embodiment, the area size ratio of the intensity distribution of the near infrared light is found on the basis of the predetermined reference value. FIG. 12 shows, for each maturity level, how the pixels having a pixel value of, for example, 80 or larger, among the pixels having the pixel value NIRS included in the image I, are distributed in the image I. As the maturity level of the bunch F rises, the density of the pixels (pixel distribution) increases. This indicates that the maturity level determination information may be obtained based on the pixel distribution on the basis of the reference value.

Portion (a) of FIG. 13A shows an image including the entirety of the bunch F that is unripe. Portion (b) of FIG. 13A shows an enlarged image I of the rectangular part, represented by the dashed line, of the image shown in portion (a) of FIG. 13A. Portion (c) of FIG. 13A is a mapping image obtained as a result of the pixel distribution of pixels in a range of predetermined pixel values being mapped based on the pixel value NIRS of the plurality of first pixels included in the image I shown in Portion (b) of FIG. 13A. Portion (a) of FIG. 13B shows an image including the entirety of the bunch F that is underripe. Portion (b) of FIG. 13B shows an enlarged image I of the rectangular part, represented by the dashed line, of the image shown in portion (a) of FIG. 13B. Portion (c) of FIG. 13B is a mapping image obtained as a result of the pixel distribution of pixels in the range of predetermined pixel values being mapped based on the pixel value NIRS of the plurality of first pixels included in the image I shown in portion (b) of FIG. 13B. Portion (a) of FIG. 13C shows an image including the entirety of the bunch F that is ripe. Portion (b) of FIG. 13C shows an enlarged image I of the rectangular part, represented by the dashed line, of the image shown in portion (a) of FIG. 13C. Portion (c) of FIG. 13C is a mapping image obtained as a result of the pixel distribution of pixels in the range of predetermined pixel values being mapped based on the pixel value NIRS of the plurality of first pixels included in the image I shown in portion (b) of FIG. 13C.

For example, it is now assumed that the entirety of the bunch F is processed with image capturing from far by the image capturing module 110 to acquire the image shown in portion (a) of FIG. 13A. In this case, as described above, the image I includes complicated information other than the bunch F, for example, the background, the shadow and the like. Such complicated information may possibly have adverse influence on the maturity level determination. In order to suppress this influence, it is preferable to perform image capturing of, for example, the rectangular part represented by the dashed line shown in portion (a) of FIG. 13A in an enlarged manner. As a result, the image I shown in portion (b) of FIG. 13A is acquired. In this case, the image capturing module 110 may include a narrow angle lens having a relatively long focal distance, or may include an optical zoom lens. Alternatively, the image capturing module 110 may have an electronic zoom function, needless to say. The rectangular part preferably includes at least three fruits.

After an image including one or a plurality of bunches F or the entirety of the oil palm tree is acquired by the image capturing module 110, the signal processing circuit 120 may extract the rectangular part represented by the dashed line from such an image by trimming. In other words, the signal processing circuit 120 may use a trimming function to acquire the image I shown in portion (b) of FIG. 13A. In this manner, in the case where, for example, an image of the entirety of the oil palm tree is captured from far, information on the fruits necessary for the maturity level determination may be obtained in a preferable manner while the above-described complicated information is eliminated. It is preferable that the image I to be trimmed also includes at least three fruits.

For performing image capturing of the bunch F or the entirety of the oil palm tree, a part of bunch F including, for example, three fruits may be automatically specified (recognized) by image recognition. Trimming may be performed in substantially the same manner. An example of usable image recognition technology may be any of a wide range of known pattern recognition technologies. It may be analyzed which of patterns corresponding to class prepared in advance (fruit, branch, leaf, etc.) matches the subject, so as to determine the class. Pattern recognition is performed by use of, for example, a trainable pattern recognition system using mathematical, geometrical and harmonic-shape descriptors. Such a system is educated so as to select a possible class by use of a knowledge base learned by contacting a large number of samples of each class prepared in advance. A training set includes thousands of basic types of images for each class. Successful pattern matching is caused when an untrained descriptor on the target matches a trained descriptor on the target. The above-described pattern recognition system is described in detail in, for example, Japanese Laid-Open Patent Publication No. 2015-046162.

The mapping image shown in portion (c) of FIG. 13A includes mapping images of three hierarchical layers I, II and III. For example, the mapping image of the hierarchical layer I includes a distribution of pixels having a gray scale value of 60 or larger and smaller than 70 among the gray scale values of 0 to 255. The mapping image of the hierarchical layer II includes a distribution of pixels having a gray scale value of 70 or larger and smaller than 80 among the gray scale values of 0 to 255. The mapping image of the hierarchical layer III includes a distribution of pixels having a gray scale value of 80 or larger. The signal processing circuit 120 may, for example, map the pixel distribution with blue to generate a blue mapping image of the hierarchical layer I, map the pixel distribution with green to generate a green mapping image of the hierarchical layer II, and map the pixel distribution with red to generate a red mapping image of the hierarchical layer III. The signal processing circuit 120 places the mapping images of the three hierarchical layers I, II and III such that the images overlap each other to generate the mapping image. However, the signal processing circuit 120 does not need to generate the color mapping images of the three hierarchical layers I, II and III. The signal processing circuit 120 merely needs to generate at least a color mapping image of the hierarchical layer III based on one threshold value (e.g., "80"). The number of the hierarchical layers may be determined in accordance with, for example, the number of maturity levels.

The signal processing circuit 120 also generates the mapping image shown in portion (c) of FIG. 13B on the underripe bunch F and the mapping image shown in portion (c) of FIG. 13C on the ripe bunch F, like the mapping image on the unripe bunch F. The mapping image shown in portion (c) of FIG. 13B is generated based on the pixel value NIRS in the image I shown in portion (b) of FIG. 13B, and includes color mapping images respectively of the three hierarchical layers I, II and III. The mapping image shown in portion (c) of FIG. 13C is generated based on the pixel value NIRS in the image I shown in portion (b) of FIG. 13C, and includes color mapping images respectively of the three hierarchical layers I, II and III.

As the maturity level of the bunch F rises, the intensity of the reflected light of the near infrared light, namely, the value of the pixel value NIRS increases. As a result, the density of the pixels of the hierarchical layer III is raised. This indicates that the maturity level of the bunch F is easily determinable by appropriately setting the threshold value for the gray scale value.

Figure 14:
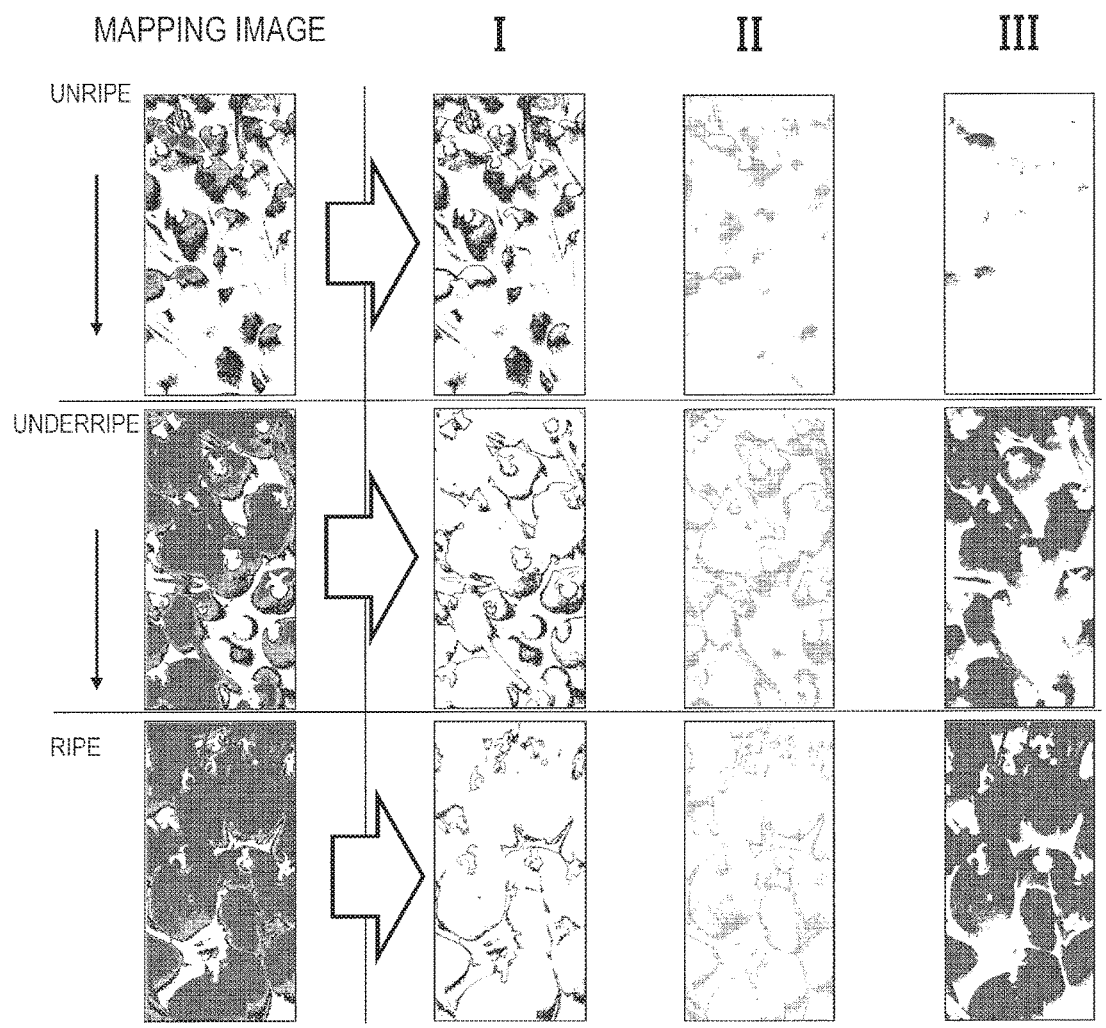
FIG. 14 shows color mapping images obtained as a result of dividing each of three mapping images of the unripe, underripe and ripe bunches F into three hierarchical layers I, II and III.

Referring to FIG. 14, the three mapping images on the unripe, underripe and ripe bunches F are each divided into the three hierarchical layers I, II and III. FIG. 14 shows the color mapping images of the respective hierarchical layers. As shown in FIG. 14, regarding the color mapping images of the hierarchical layer I, the density of the pixels is highest in the color mapping image on the unripe bunch F and lowest in the color mapping image on the ripe bunch F. Regarding the color mapping images of the hierarchical layer II, the density of the pixels is highest in the color mapping image on the underripe bunch F and lowest in the color mapping image on the unripe bunch F. Regarding the color mapping images of the hierarchical layer III, the density of the pixels is highest in the color mapping image on the ripe bunch F and lowest in the color mapping image on the unripe bunch F.

The pixel distribution of each hierarchical layer corresponds to the area size ratio AR of the intensity distribution of the near infrared light on the basis of the predetermined reference value. Specifically, the area size ratio AR is the ratio of the number N1 of pixels fulfilling a condition for the reference value among the plurality of first pixels included in the image I with respect to the number M1 of the plurality of first pixels. For example, the lower limit of the reference value (lower-limit threshold value) and the upper limit of the reference value (upper-limit threshold value) used for the hierarchical layer I are respectively 60 and 70. The lower limit and the upper limit of the reference value used for the hierarchical layer II are respectively 70 and 80. The lower limit of the reference value used for the hierarchical layer III is 80. The upper limit is not set. An appropriate reference value may be set, so that the maturity level of the bunch F is determined based on the density of the pixels, namely, the area size ratio AR.

Figure 15:
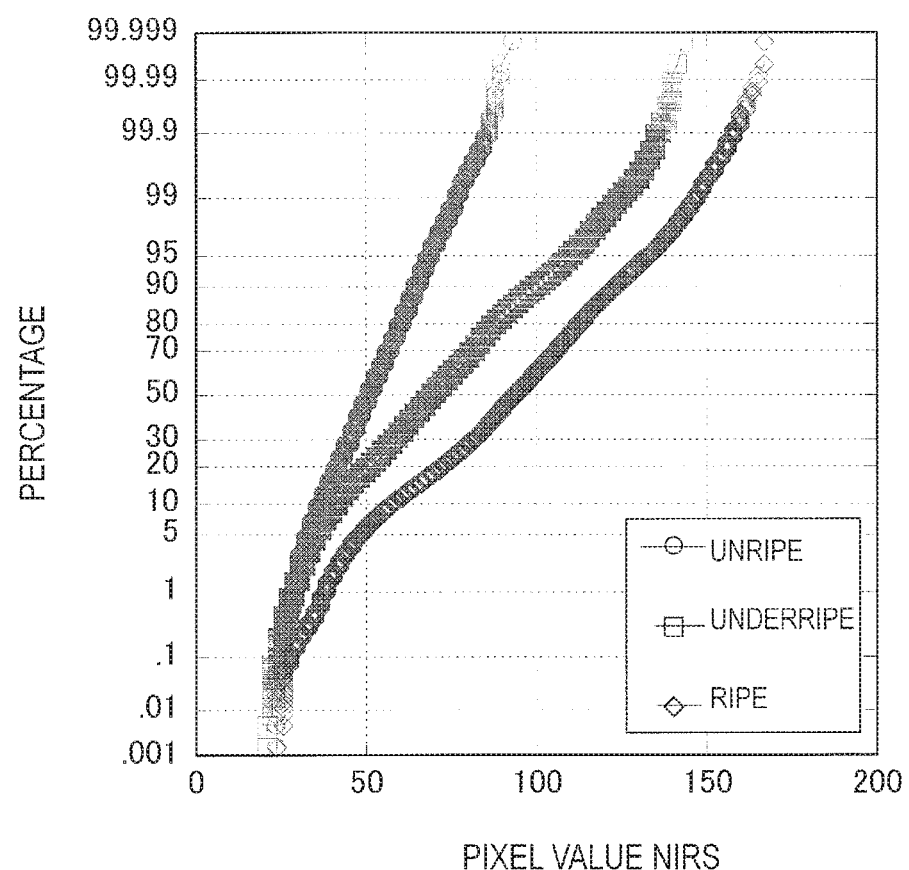
FIG. 15 is a graph obtained as a result of performing normal probability plotting of a signal strength of near infrared light reflected by each of the unripe, underripe and ripe bunches F.

FIG. 15 is a graph obtained as a result of performing normal probability plotting of the signal strength of the near infrared light (i.e., pixel value NIRS) reflected by each of the unripe, underripe and ripe bunches F. The normal probability plot visually represents how close the sample data is to the normal distribution. In the normal probability plot, data conforming to the normal distribution is arranged linearly. From this, parameters such as the average value, the standard deviation, the representative value and the like may be estimated. The sample data in this embodiment is the pixel value NIRS of the plurality of first pixels included in the image I. The horizontal axis of the graph represents the pixel value (value of 0 to 255), and the vertical axis represents the cumulative frequency percentage (%) represented by logarithm.

The cumulative frequency percentage (%) is found from expression (1).

Cumulative frequency percentage (%)=(100×cumulative frequency)/($n$+1)   expression (1)

In expression (1), the cumulative frequency corresponds to a value obtained by accumulating the frequency from the smallest value of the frequency, namely, the left side of the histogram. n is the number of samples, and is equal to the number M1 of the plurality of first pixels.

As shown in FIG. 15, independent normal probability plots are obtained for the respective maturity levels. It is seen that as the maturity level of the bunch F rises, the normal probability plot is shifted rightward, and as a result, the pixel value NIRS for a cumulative frequency percentage of 50% increases. The pixel value at the cumulative frequency percentage of 50% is a representative value of the pixel value NIRS. In the normal distribution, the average value is equal to the representative value. The normal probability plot is effective for determining the above-described threshold values as the upper limit and the lower limit. For example, these threshold values may be determined based on the representative value by referring to the normal probability plot.

Figure 16:
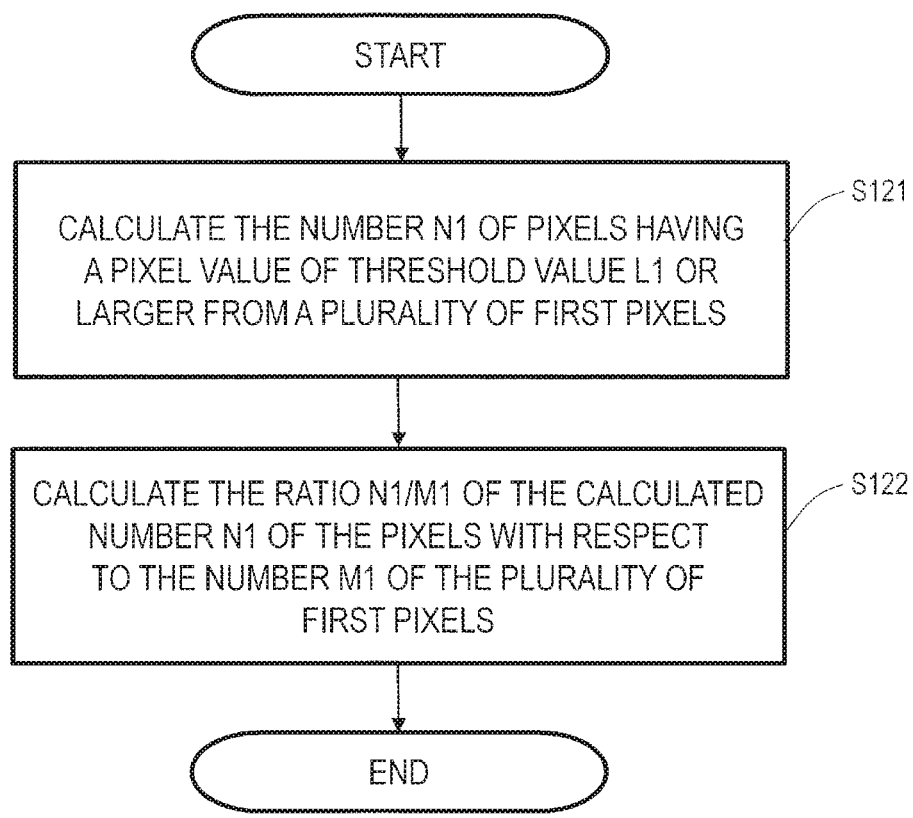
FIG. 16 is a flowchart showing a procedure of calculating an area size ratio of an intensity distribution of near infrared light (step S120) in detail.

FIG. 16 shows a procedure of calculating the area size ratio of the intensity distribution of the near infrared light (step S120) in detail.

The signal processing circuit 120, specifically, the area size ratio computation section 121 (see FIG. 8) of the signal processing circuit 120, finds the area size AR of the intensity distribution of the near infrared light on the basis of a predetermined reference value. Specifically, in step S121, the area size ratio computation section 121 calculates the number N1 of pixels having a pixel value larger than, or equal to, a threshold value L1 from the plurality of first pixels included in the image I. For example, for the hierarchical layer III shown in FIG. 14, "80" may be set as the threshold value L1. As a result of computation, the number of the pixels having a pixel value of "80" or larger is N1. Alternatively, N1 may be the number of pixels having a pixel value smaller than, or equal to, the threshold value L1, and in step S121, the area size ratio computation section 121 may calculate the number N1 from the plurality of first pixels included in the image I.

Next, in step S122, the area size ratio computation section 121 finds the ratio N1/M1, namely, the ratio the calculated number N1 of the pixels with respect to the number M1 of the plurality of first pixels. It is now assumed that the image I is formed of only the plurality of first pixels. In this case, if the angle of view is narrow, the shadow between the fruits may possibly influence the maturity level determination. Therefore, it is preferable that a further threshold value is provided, so that the number of first pixels having a pixel value larger than, or equal to, the further threshold value (e.g., "10") is set as M1 to find the ratio N1/M1.

Now, FIG. 10 will be referred to again.

The maturity level determination information generation section 122 of the signal processing circuit 120 generates maturity level determination information in accordance with the area size ratio AR (step S130). Specifically, the maturity level determination information generation section 122 generates the maturity level determination information in accordance with a result of comparing the ratio N1/M1 against a threshold value R1.

Figure 17:
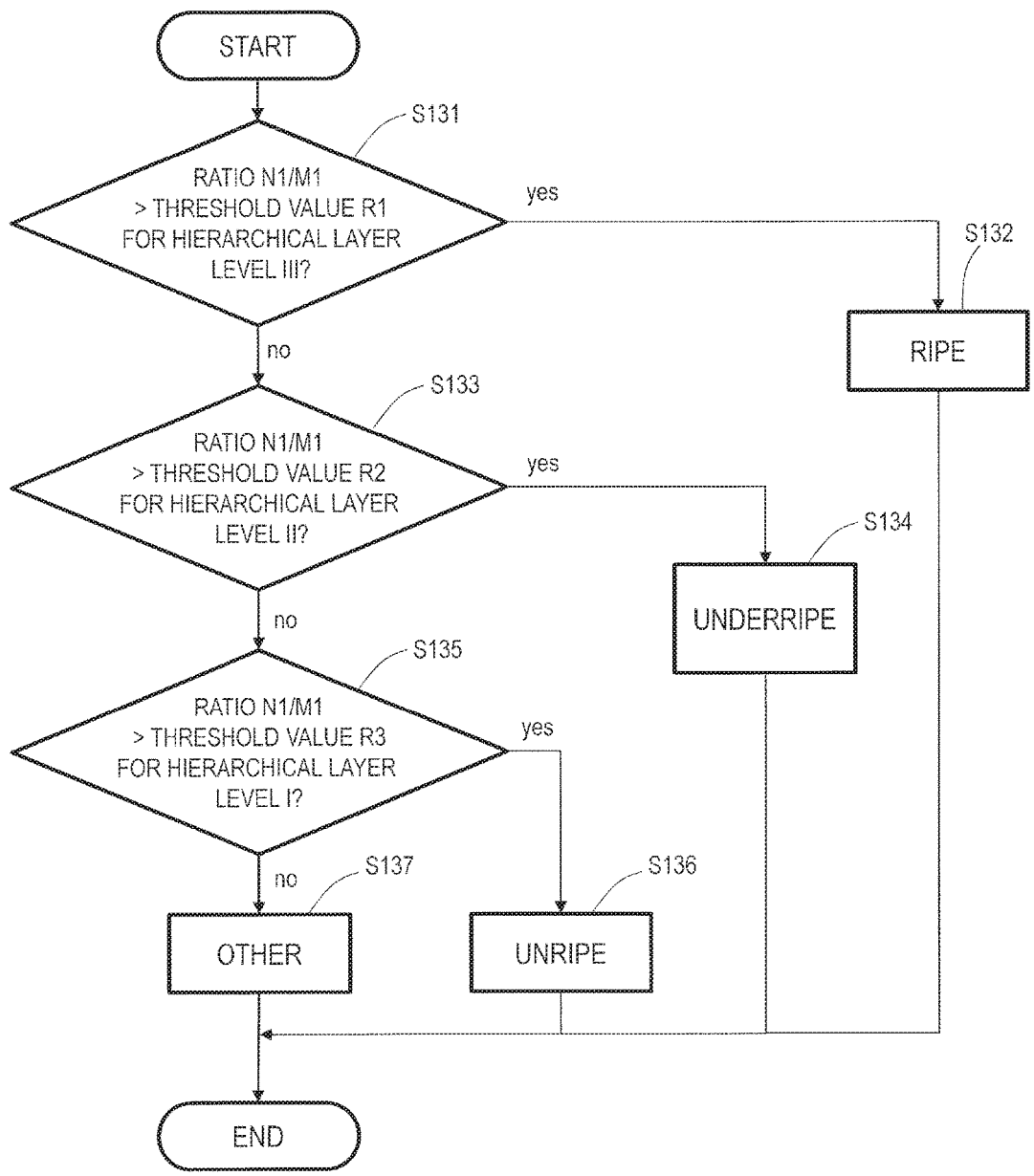
FIG. 17 is a flowchart showing a specific processing procedure in step S130 of generating the maturity level determination information in detail.

FIG. 17 shows a specific processing procedure in step S130 of generating the maturity level determination information in detail. First, a procedure of determining whether the maturity level of the bunch F is "ripe" or not will be described. In step S131, the maturity level determination information generation section 122 determines whether the ratio N1/M1 calculated for the hierarchical layer III is larger than the threshold value R1 or not. The threshold value R1 is appropriately determined by the designing specifications or the like, and is, for example, stored in advance on the storage medium (internal ROM) 123 of the signal processing circuit 120. All the threshold values described in this specification, including the threshold value R1, are stored on the storage medium 123. In the case where the ratio N1/M1 is larger than the threshold value R1 in step S131, the maturity level determination information generation section 122 generates maturity level determination information representing "ripe" (step S132). In the case where the ratio N1/M1 is smaller than, or equal to, the threshold value R1, the maturity level determination information generation section 122 generates maturity level determination information representing, for example, "unripe". The maturity level determination information may be represented by, for example, a 1-bit signal, where "0" may be assigned to "unripe" and "1" may be assigned to "ripe". With the above-described procedure, the maturity level determination information representing whether the maturity level of the bunch F is "ripe" or not is obtained.

For example, it may be further determined whether or not the maturity level is "underripe" or "unripe". Referring to FIG. 17, in the case where the ratio N1/M1 is determined as being smaller than, or equal to, the threshold value R1 in step S131, it is at least known that the maturity level is not "ripe". In step S133, the maturity level determination information generation section 122 finds the ratio N1/M1 for the hierarchical layer II and compares the ratio against a threshold value R2.

Specifically, for the hierarchical layer II, the maturity level determination information generation section 122 calculates, among the plurality of first pixels, the number N1 of pixels having a pixel value larger than, or equal to, the lower limit of a threshold value L2 and smaller than the upper limit of the threshold value L2. As described above, for example, the lower limit of the threshold value L2 may be set to "70" and the upper limit of the threshold value L2 may be set to "80". For the hierarchical layer II, the maturity level determination information generation section 122 finds the ratio N1/M1, namely, the ratio the calculated number N1 of the pixels with respect to the number M1 of the plurality of first pixels.

In step S133, the maturity level determination information generation section 122 determines whether the ratio N1/M1 calculated for the hierarchical layer II is larger than the threshold value R2 or not. In the case where the ratio N1/M1 is larger than the threshold value R2, the maturity level determination information generation section 122 generates maturity level determination information representing "underripe" in step S134. In the case where the ratio N1/M1 is smaller than, or equal to, the threshold value R2, the procedure goes to step S135.

In step S135, the maturity level determination information generation section 122 finds the ratio N1/M1 for the hierarchical layer I and compares the ratio against a threshold value R3. Specifically, for the hierarchical layer I, the maturity level determination information generation section 122 calculates, among the plurality of first pixels, the number N1 of pixels having a pixel value larger than, or equal to, the lower limit of a threshold value L3 and smaller than the upper limit of the threshold value L3. As described above, for example, the lower limit of the threshold value L3 may be set to "60" and the upper limit of the threshold value L3 may be set to "70". For the hierarchical layer I, the maturity level determination information generation portion 122 finds the ratio N1/M1, namely, the ratio the calculated number N1 of the pixels with respect to the number M1 of the plurality of first pixels.

In step S135, the maturity level determination information generation section 122 determines whether the ratio N1/M1 calculated for the hierarchical layer I is larger than the threshold value R3 or not. In the case where the ratio N1/M1 is larger than the threshold value R3, the maturity level determination information generation section 122 generates maturity level determination information representing "unripe" in step S136. In the case where the ratio N1/M1 is smaller than, or equal to, the threshold value R3, the maturity level determination information generation section 122 generates maturity level information representing, for example, "other" in step S137. The maturity level determination information may be represented by, for example, a 2-bit signal, where "11" may be assigned to "ripe", "10" may be assigned to "underripe", "01" may be assigned to "unripe", and "00" may be assigned to "other". In this manner, the maturity level determination information representing "underripe" or "unripe" may be generated in addition to the maturity level determination information representing "ripe".

Now, FIG. 9 will be referred to again.

The maturity determination device 100 generates a control signal for turning on or off the driving of the harvesting means 600 based on the determination result on the maturity level (step S200). Specifically, the control signal generation section 124 of the signal processing circuit 120 generates the control signal. In the case where it is determined that the maturity level has reached a predetermined level, the control signal generation section 124 generates a control signal for turning on the driving of the harvesting means 600. In the case where it is determined that the maturity level has not reached the predetermined level, the control signal generation section 124 generates a control signal for turning off the driving of the harvesting means 600. The "predetermined level" may be, for example, "ripe". In the case where the above-described 2-bit signal representing the maturity level determination information is "11", the control signal generation section 124 generates a control signal for turning on the driving of the harvesting means 600. The control signal is, for example, a 1-bit signal, and the control signal for turning on the driving may be assigned to "1". In the case where the above-described 2-bit signal representing the maturity level determination information is a value other than "11", the control signal generation section 124 generates a control signal for turning off the driving of the harvesting means 600. The control signal for turning off the driving may be assigned to "0". In other words, the control signal is a signal that is asserted in the case where it is determined that the maturity level is "ripe".

Next, the controller 200 receives the control signal output from the maturity determination device 100 and determines whether or not to supply power for driving the harvesting means 600 to the harvesting means 600 in accordance with the control signal (step S300). In other words, the controller 200 determines whether or not to permit the harvesting means 600 to be driven (whether the operation of the harvesting means 600 is to be turned on or off) in accordance with the control signal. Specifically, in the case where the control signal indicates "1", namely, in the case where the control signal is asserted, the controller 200 determines to supply the power to the harvesting means 600. In other words, in the case where the control signal is asserted, the controller 200 permits the harvesting means 600 to be driven. By contrast, in the case where the control signal indicates "0", the controller 200 determines not to supply the power to the harvesting means 600. In other words, in the case where the control signal is in a negated state, the controller 200 does not permit the harvesting means 600 to be driven.

Next, in step S400, the power source 300 starts supplying the power in accordance with the determination made by the controller 200 to supply the power. In the case where the harvesting means 600 is permitted to be driven, the supply of the power from the power source 300 to the harvesting means 600 is started (step S500), and the harvesting means 600 is driven by the power (step S600). As a result, the harvesting means 600 is in a state of capable of reaping the bunch F. The harvesting apparatus 1000 may be in one of two states. One is state A, in which the harvesting apparatus 1000 is not capable of harvesting the bunch F, and the other is state B, in which the harvesting apparatus 1000 is capable of harvesting the bunch F. In the case where the control signal from the maturity determination device 100 is asserted, the state of the harvesting apparatus 1000 is transferred from state A to state B.

In this manner, it is determined whether or not to operate the harvesting means 600 in accordance with the determination result on the maturity level. The timing to harvest the bunch F is determined with high precision without decreasing the efficiency of the harvesting work. As a result, the bunch F to be harvested is properly harvested. In addition, the bunch F not to be harvested is prevented from being harvested by a human error.

As shown in FIG. 2, the controller 200 directly controls the power source 300 to be on or off. In the case where the control signal from the maturity determination device 100 is in a negated state, the controller 200 keeps the power source 300 in an off state. In the case where the control signal is asserted, the controller 200 turns on the power source 300. In the case where, for example, a gasoline engine is used as the power source 300, the gasoline engine is started in response to the control signal. In the case where, for example, an electric motor is used as the power source 300, when the supply of the electric power is started from a battery to the electric motor via, for example, an inverter in response to the control signal, the electric motor is driven.

According to this structure, the power source 300 is turned on only in the case where the maturity level has reached a predetermined level. The user of the harvesting apparatus 1000 may optionally set a predetermined condition under which the harvesting is permitted, for the determined maturity level. Since the power source 300 is turned on only in the case where the set condition is fulfilled, only the bunch F which has reached the predetermined level is harvested. In the case where the predetermined condition under which the harvesting is permitted is not fulfilled, the power source 300 is turned off with certainty. In this manner, harvesting by a human error is prevented.

The harvesting apparatus 1000 may have an operation mode in which state B is maintained only for a predetermined time period (e.g., 15 minutes). Namely, the harvesting means 600 is permitted to be driven only for the predetermined time period. The operation mode is set by, for example, an input by a key (not shown) or the like. For example, it is preferable that the harvesting apparatus 1000 set such that only the administrator of the harvesting work (administrator of the plantation) is permitted to set the operation mode but the harvesting worker is not permitted to set the operation mode.

Unless the harvesting means 600 is permitted to be driven, the power is not supplied from the power source 300 to the harvesting means 600 (step S700). As a result, the harvesting apparatus 1000 is kept in state A. In this manner, it may be determined whether or not to operate the harvesting means 600 by directly controlling the power source 300 in accordance with the control signal.

Figure 18:
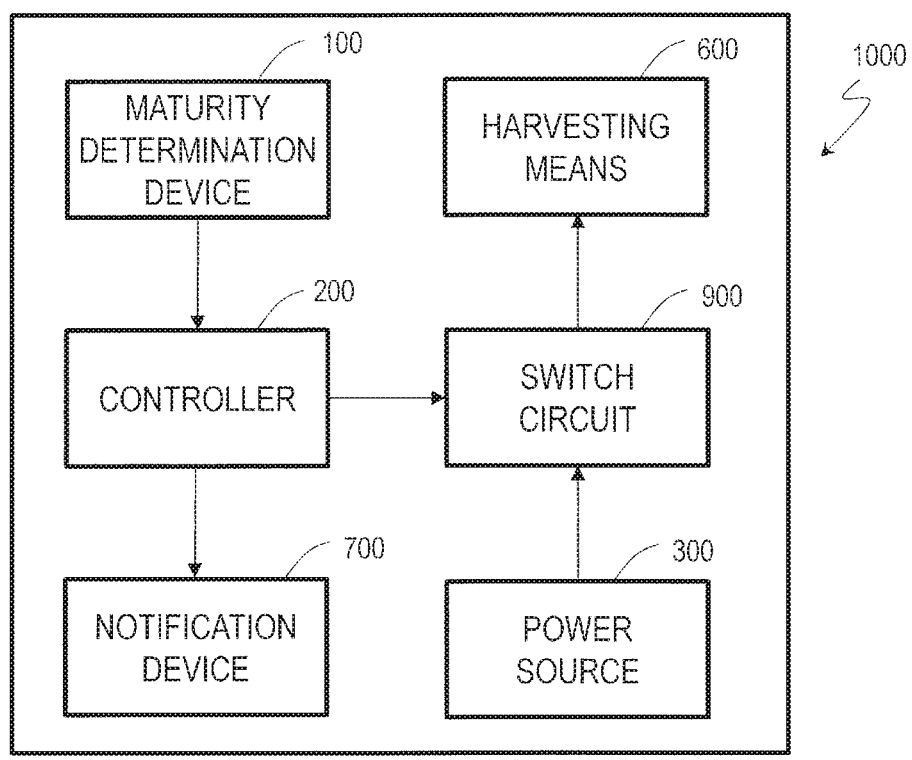
FIG. 18 is a block diagram schematically showing still another example of hardware structure of the harvesting apparatus 1000.

FIG. 18 schematically shows still another example of hardware structure of the harvesting apparatus 1000. In this example, the harvesting apparatus 1000 further includes a switch circuit 900. The switch circuit 900 includes, for example, a relay switch, and switches the harvesting apparatus 1000 between a state of supplying power from the power source 300 to the harvesting means 600 and a state of blocking the supply. This switching may be controlled by the controller 200. In the case where the control signal from the maturity determination device 100 is in a negated state, the controller 200 turns off the relay switch of the switch circuit 900. As a result, the supply of the power from the power source 300 to the harvesting means 600 is stopped. By contrast, in the case where the control signal from the maturity determination device 100 is asserted, the controller 200 turns on the relay switch of the switch circuit 900. As a result, the power is supplied from the power source 300 to the harvesting means 600. In this manner, the switch circuit 900 may be used to control on whether the power is to be supplied or not, and thus the harvesting apparatus 1000 is switched between state A and state B.

The controller 200 generates a driving signal for driving the notification device 700 in accordance with the maturity level determination information. For example, the notification device 700 may include an LED. In the case where the maturity level determination information represents "ripe", the controller 200 generates a driving signal for lighting up the LED (signal for turning on the LED). In the case where the maturity level determination information represents a level other than "ripe", the controller 200 does not generate a driving signal for lighting up the LED. The controller 200 may include a plurality of LEDs of different light colors. In the case where the maturity level determination information represents one of various maturity levels (e.g., "ripe", "underripe" and "unripe"), the controller 200 may generate a driving signal for lighting up one of the plurality of LEDs in accordance with the maturity level. Such an arrangement allows the harvesting worker to recognize the maturity level of the bunch F in accordance with the light color of the LED.

The notification device 700 may include, for example, a speaker. In the case where the maturity level determination information represents "ripe", the controller 200 generates a driving signal for allowing the speaker to output a sound (signal for turning on the speaker). In the case where the maturity level determination information represents a level other than "ripe", the controller 200 does not generate a driving signal for allowing the speaker to output a sound. In the case where the maturity level determination information represents one of various maturity levels, the controller 200 may drive the speaker to output a sound having one of various loudness levels in accordance with the maturity level.

The notification device 700 may include, for example, a vibrator. In the case where the maturity level determination information represents "ripe", the controller 200 generates a driving signal for vibrating the vibrator (signal for turning on the vibrator). In the case where the maturity level determination information represents a level other than "ripe", the controller 200 does not generate a driving signal for vibrating the vibrator. In the case where the maturity level determination information represents one of various maturity levels, the controller 200 may drive the vibrator to vibrate in one of various strength levels or one of various vibration patterns in accordance with the maturity level.

The notification device 700 may include, for example, a liquid crystal display. In the case where the maturity level determination information represents "ripe", the controller 200 generates a driving signal for allowing the liquid crystal display to display letter information of "ripe". In the case where the maturity level determination information represents a level other than "ripe", the controller 200 generates a driving signal for allowing the liquid crystal display to display letter information of "not ripe". The liquid crystal display may display a signal such as "○" or "×" instead of the letter information, or may provide display in different colors in accordance with the maturity level.

The maturity determination device 100 (or the controller 200) may determine whether the bunch F is harvestable or not based on the maturity level determination information. It is now assumed that there are, for example, four maturity levels "ripe", "slightly ripe", "underripe" and "unripe". For example, in the case where the maturity level determination information represents "ripe" or "slightly ripe", the maturity determination device 100 may determine that the bunch F is "harvestable". In the case where the maturity level determination information represents "underripe" or "unripe", the maturity determination device 100 may determine that the bunch F is "not harvestable".

The notification device 700 may notify whether the bunch F is harvestable or not based on the determination result on whether the bunch F is harvestable or not. In the case where the maturity determination device 100 determines that the bunch F is not harvestable, the notification device 700 notifies that the bunch F should not be harvested. In this case, the speaker may be controlled to output a sound, or the liquid crystal display may be controlled to display a warning message that the bunch F should not be harvested. For example, the liquid crystal display may display letter information of "Do not harvest" or the like. In the case where the maturity determination device 100 determines that the bunch F is harvestable, the liquid crystal display may display letter information of "Harvesting OK" or the like. Such a display directly conveys the information on whether the bunch F is harvestable or not and thus provides a better support to the harvesting worker.

The harvesting apparatus 1000 has a "maturity level determination mode", in which the maturity determination device 100 is started to determine the maturity level. The harvesting apparatus 1000 may have another operation mode, for example, a "non-maturity level determination mode", in which fronds or limbs around the bunch F are reaped without starting the maturity determination device 100. When the "maturity level determination mode" is set, the harvesting apparatus 1000 operates in accordance with the flow shown in FIG. 9. The harvesting apparatus 1000 may be set such that when the "non-maturity level determination mode" is set, the supply of power from the power source 300 to the harvesting means 600 is permitted. The operation mode is set manually by an input by a key (not shown).

Figure 19:
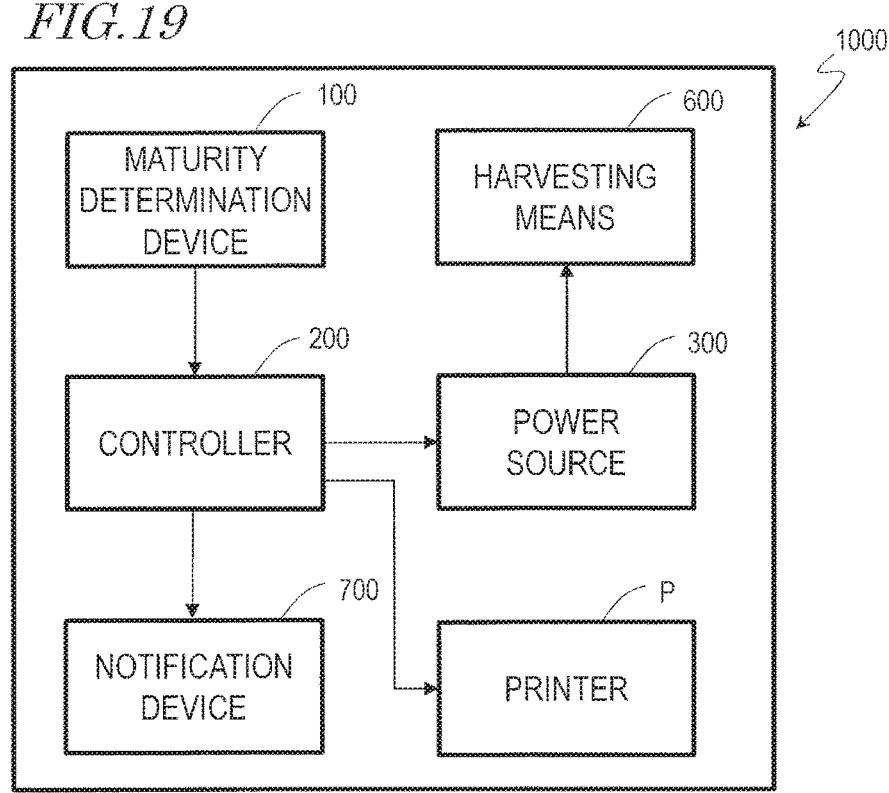
FIG. 19 is a block diagram schematically showing still another example of hardware structure of the harvesting apparatus 1000.

FIG. 19 schematically shows still another example of hardware structure of the harvesting apparatus 1000. In this example, the harvesting apparatus 1000 further includes a printer P. The printer P outputs, for example, a printed item having the maturity level of the bunch F, an image of which has been captured, printed thereon. For example, the printer P may output a printed item having the letters "ripe" or "harvestable" printed thereon when the maturity level is determined as being "ripe" or only when the bunch F is determined as being harvestable. The harvesting worker reaps the ripe bunch F and then puts the printed item output by the printer P on the reaped bunch F. The administrator may check the printed item to confirm that the harvesting worker operated the harvesting apparatus 1000 based on the determination result provided by the maturity determination device 100. In the case where the harvesting worker sets the operation mode of the harvesting apparatus 1000 to the "maturity level determination mode" in an attempt to harvest the bunch F but the bunch F is determined as not being harvestable at the current time, the harvesting worker may switch the operation mode to the "non-maturity level determination mode" to reap the fronds and the limbs. Thus, the harvesting worker may prepare to reap the bunch F the next time. In this manner, the amount of the reaping work is decreased the next time the bunch F is harvested.

In this embodiment, a series of operations from the maturity level determination on the bunch F to the harvesting of the bunch F are performed completely automatically under the control of the controller 200. Therefore, the timing to harvest the bunch F is determined highly precisely in accordance with the maturity level without decreasing the efficiency of the harvesting work. Since the operation of the harvesting means 600 is changed in accordance with the timing to harvest the bunch F, the content of an ingredient in the bunch F (e.g., palm oil) is increased (maximized). The increase in the content increases the production amount. In addition, the harvesting worker is prevented from harvesting, by an error, a bunch F that is not ripe, namely, not to be harvested. As a result, the administrator may administrate the harvest more thoroughly and thus suppress the productivity from decreasing.

(Embodiment 2)

A harvesting apparatus 1000A in this embodiment includes a lever (or a switch) L, for turning on or off an electric power supply of the power source 300, provided in the handle 400, unlike the harvesting apparatus 1000 in embodiment 1. Hereinafter, a structure and an operation of the harvesting apparatus 1000A will be described mainly regarding differences from the harvesting apparatus 1000 in embodiment 1.

[Structure of the Harvesting Apparatus 1000A]

Figure 20:
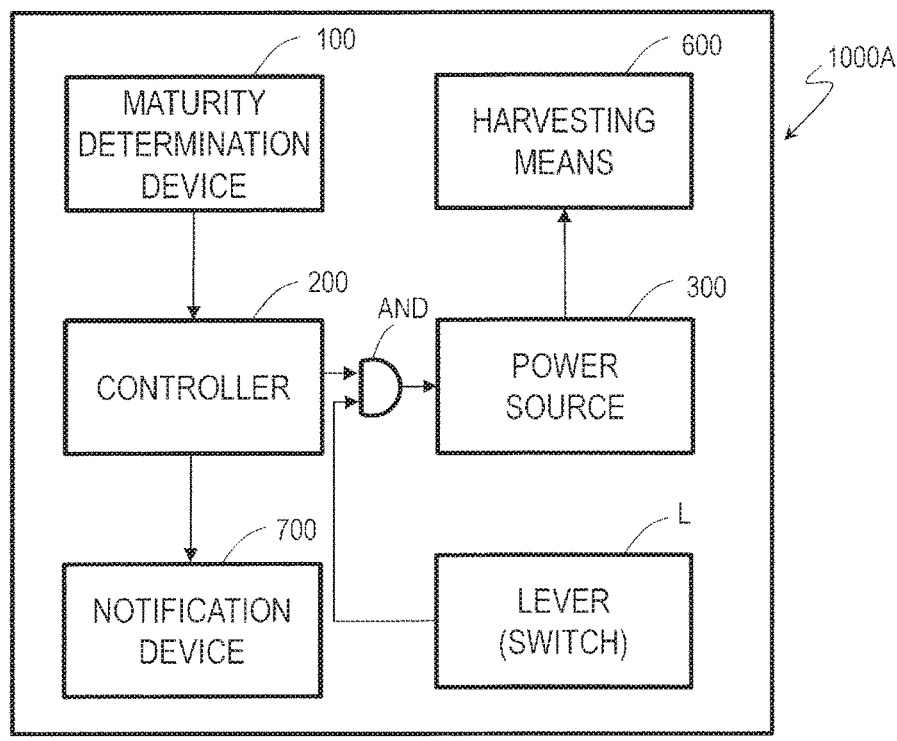
FIG. 20 is a block diagram schematically showing an example of hardware structure of a harvesting apparatus 1000A in embodiment 2.

FIG. 20 schematically shows an example of hardware structure of the harvesting apparatus 1000A in this embodiment.

The harvesting apparatus 1000A further includes the lever (or switch) L for turning on or off the electric power supply of the power source 300. As shown in FIG. 20, a signal output from the lever L and a control signal, for turning on or off the power source 300, output from the controller 200 are input to, for example, an AND gate. An output from the AND gate is input to the power source 300.

For example, when the harvesting worker pulls the lever L in an attempt to operate the harvesting apparatus 1000A, this action triggers a high level signal for turning on the power source 300 to be output from the lever L to the AND gate. However, in the case where, for example, the control signal output from the power source 300 is in a negated state, namely, in the case where the harvesting means 600 is not permitted to be driven, even if the harvesting worker pulls the lever L, the signal output from the lever L is masked by the AND gate. Therefore, the power source 300 is kept off. By contrast, in the case where the control signal output from the power source 300 is asserted, if the harvesting worker pulls the lever L, the power source 300 is turned on to drive the harvesting means 600.

According to this structure, unless the controller 200 permits the harvesting means 600 to be driven, the harvesting means 600 is not operated even if the harvesting worker pulls the lever L. Therefore, harvesting by a human error is prevented.

Although not shown, the harvesting apparatus 1000A may include the switch circuit 900, like the harvesting apparatus 1000 in embodiment 1. In this case, the AND gate may be connected with the switch circuit 900. A combination of the switch circuit 900 and the AND gate may also effectively prevent harvesting from being performed by a human error.

[Operation of Harvesting Apparatus 1000A]

The maturity level determination usable by the harvesting method in an embodiment according to the present invention is not limited to being performed by the method described in embodiment 1. For example, the following maturity level determination may be preferably usable.

FIG. 21 shows a procedure by which the maturity determination device 100 of the harvesting apparatus 1000A in this embodiment generates maturity level determination information in detail. Hereinafter, the procedure will be described mainly regarding differences from the maturity level determination described in embodiment 1.

Step S110A is substantially the same as step S110 described in embodiment 1 with reference to FIG. 10. In this embodiment, the image I including the intensity distribution of at least the near infrared light and the blue light is analyzed to determine the maturity level.

The signal processing circuit 120 calculates the area size ratio of the intensity distribution of the near infrared light in the received image I in consideration of the intensity distribution of the blue light (step S120A). The image I includes at least a plurality of first pixels having information representing the intensity distribution of the near infrared light and a plurality of second pixels having information representing the intensity distribution of the blue light. With the maturity level determination in this embodiment, the area size ratio of the intensity distribution of the near infrared light is found on the basis of a predetermined reference value and in consideration of the intensity distribution of the blue light.

Portion (a) of FIG. 22A shows an image including the entirety of the bunch F that is unripe. Portion (b) of FIG. 22A shows an enlarged image I of the rectangular part, represented by the dashed line, of the image shown in portion (a) of FIG. 22A. Portion (c) of FIG. 22A is a mapping image obtained as a result of the pixel distribution of pixels in a range of predetermined pixel values being mapped based on the pixel value NIRS in the image I shown in portion (b) of FIG. 22A. Portion (d) of FIG. 22A is a mapping image obtained as a result of the pixel distribution of pixels in the range of predetermined pixel values being mapped based on a quotient value obtained by dividing the pixel value NIRS in the image I shown in portion (b) of FIG. 22A by the pixel value BLUS.

Portion (a) of FIG. 22B shows an image including the entirety of the bunch F that is underripe. Portion (b) of FIG. 22B shows an enlarged image I of the rectangular part, represented by the dashed line, of the image shown in portion (a) of FIG. 22B. Portion (c) of FIG. 22B is a mapping image obtained as a result of the pixel distribution of pixels in the range of predetermined pixel values being mapped based on the pixel value NIRS in the image I shown in portion (b) of FIG. 22B. Portion (d) of FIG. 22B is a mapping image obtained as a result of the pixel distribution of pixels in the range of predetermined pixel values being mapped based on a quotient value obtained by dividing the pixel value NIRS in the image I shown in portion (b) of FIG. 22B by the pixel value BLUS.

Portion (a) of FIG. 22C shows an image including the entirety of the bunch F that is ripe. Portion (b) of FIG. 22C shows an enlarged image I of the rectangular part, represented by the dashed line, of the image shown in portion (a) of FIG. 22C. Portion (c) of FIG. 22C is a mapping image obtained as a result of the pixel distribution of pixels in the range of predetermined pixel values being mapped based on the pixel value NIRS in the image I shown in portion (b) of FIG. 22C. Portion (d) of FIG. 22C is a mapping image obtained as a result of the pixel distribution of pixels in the range of predetermined pixel values being mapped based on a quotient value obtained by dividing the pixel value NIRS in the image I shown in portion (b) of FIG. 22C by the pixel value BLUS.

The mapping image shown in portion (c) of FIG. 22A is generated based on the pixel value NIRS included in the image I, and includes the mapping images of three hierarchical layers I, II and III. For example, the mapping image of the hierarchical layer I includes a distribution of pixels having a gray scale value of 60 or larger and smaller than 70 among the gray scale values of 0 to 255. The mapping image of the hierarchical layer II includes a distribution of pixels having a gray scale value of 70 or larger and smaller than 80 among the gray scale values of 0 to 255. The mapping image of the hierarchical layer III includes a distribution of pixels having a gray scale value of 80 or larger. The mapping images shown in portions (c) of FIG. 22B and FIG. 22C also each include the mapping images of three hierarchical layers I, II and III.

The mapping image shown in portion (d) of FIG. 22A is generated based on the quotient value obtained by dividing the pixel value NIRS in the image I by the pixel value BLUS, and includes the mapping images of three hierarchical layers I, II and III. For example, the mapping image of the hierarchical layer I includes a distribution of pixels having a gray scale value of 60 or larger and smaller than 70 among the gray scale values of 0 to 255. The mapping image of the hierarchical layer II includes a distribution of pixels having a gray scale value of 70 or larger and smaller than 80 among the gray scale values of 0 to 255. The mapping image of the hierarchical layer III includes a distribution of pixels having a gray scale value of 80 or larger. The mapping images shown in portions (d) of FIG. 22B and FIG. 22C also each include the mapping images of three hierarchical layers I, II and III.

In this embodiment, the signal processing circuit 120 generates the mapping image shown in portion (d) of FIG. 22A for the unripe bunch F. The signal processing circuit 120 also generates the mapping images shown in portions (d) of FIG. 22B and FIG. 22C respectively for the underripe and unripe bunches F. The signal processing circuit 120 may determine the maturity level by use of these mapping images.

As can be seen from the mapping images shown in portions (c) of FIG. 22A, FIG. 22B and FIG. 22C, as the maturity level of the bunch F rises, the intensity of the reflected light of the near infrared light, namely, the value of the pixel value NIRS increases. As a result, the density of the pixels of the hierarchical layer level III is raised. However, the pixel distributions in the mapping images on the underripe bunch F and the ripe bunch F do not appear to be much different from each other because of the influence of the near infrared light in the external disturbing light (mainly, sunlight).

As shown in, for example, FIG. 11, the reflectance of the blue light does not vary almost at all in accordance with the maturity level, and therefore, is usable as intensity reference for the reflected light for suppressing the influence of the sunlight. In the mapping images shown in portions (d) of FIG. 22A, FIG. 22B and FIG. 22C, a sufficient difference is easily seen between the pixel distributions on the mapping images on the underripe bunch F and the ripe bunch F. A reason for this is that these mapping images are obtained based on a quotient value obtained by dividing the pixel value NIRS in the image I by the pixel value BLUS, and thus the influence of the sunlight is suppressed. This indicates that the maturity level of the bunch F is determinable with high precision by appropriately setting the threshold value for the gray scale value for a mapping image generated based on the quotient value.

Now, it will be discussed on generating a mapping image based on a difference value obtained by subtracting the pixel value BLUS in the image I from the pixel value NIRS. In this case, it is not possible to determine, with high precision, the maturity level of the bunch F with the influence of the sunlight being suppressed. It is known that, for example, the spectrum of the sunlight significantly varies between in a sunlit area and in a shadow area or between on a cloudy day and on a day of good weather. It is known that the intensity of light of a visible wavelength band on a cloudy day is about ⅓ of that of a day of good weather, whereas the intensity of the near infrared light is not different almost at all. On a day of good weather and also on a cloudy day, the intensity of the blue light is several times as high as the intensity of the near infrared light. In other words, the intensity of the blue light incident on the bunch F is several times as high as the intensity of the near infrared light incident on the bunch F. By contrast, the intensity of the near infrared light reflected by the bunch F is several times as high as the intensity of the blue light reflected by the bunch F.

At least in a sunlit area, the intensity of the blue light included in the external disturbing light is high. Therefore, in the case where the pixel value BLUS included in the image I is subtracted from the pixel value NIRS, a difference in accordance with the maturity level is not seen in the difference value, namely, the post-subtraction signal. By contrast, in this embodiment, the pixel value NIRS included in the image I is divided by the pixel value BLUS. In this case, even though the intensity of the blue light included in the external disturbing light is high, the post-division signal still includes a signal component representing information in accordance with the maturity level. Such a signal component may be amplified by, for example, the signal processing.

Figure 23:
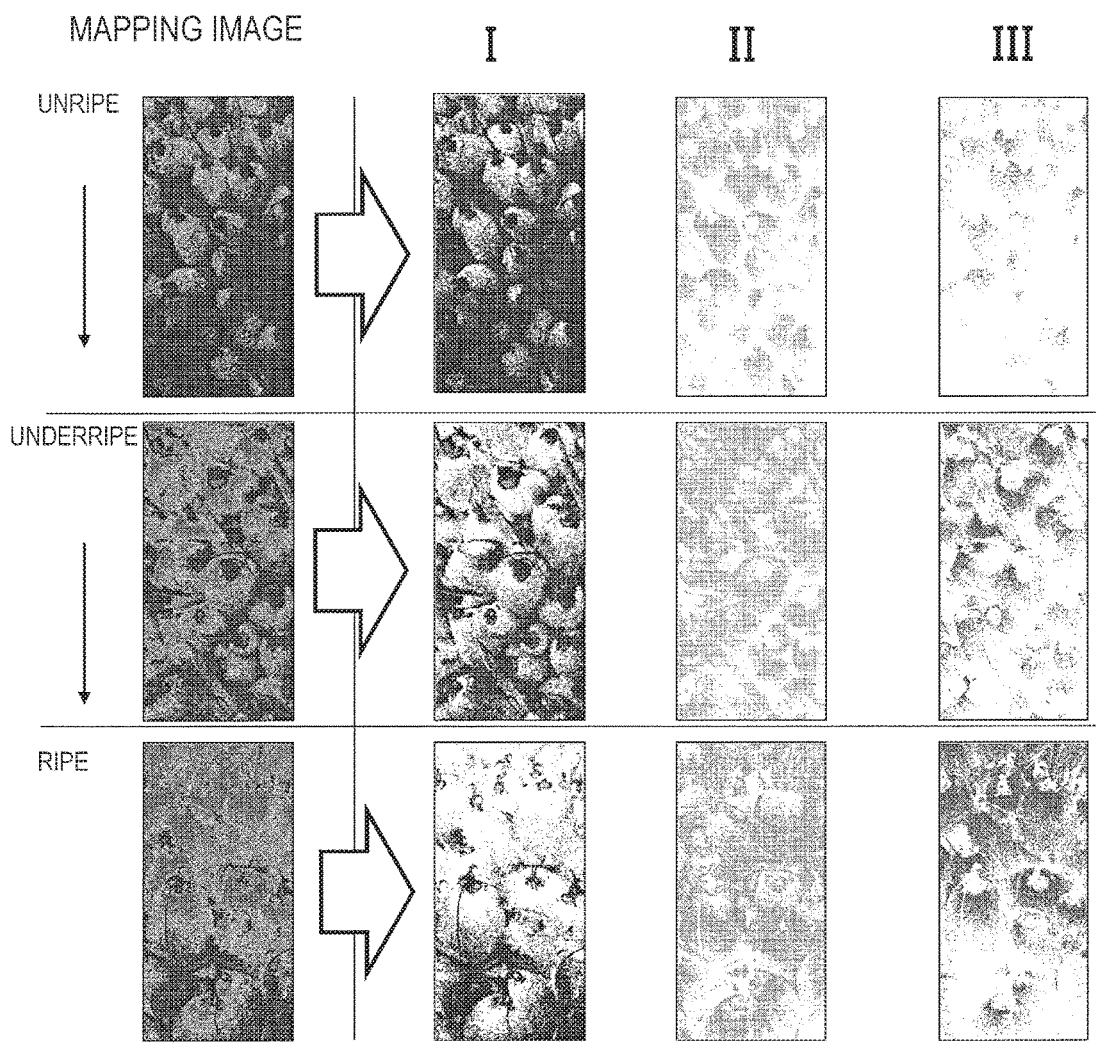
FIG. 23 shows color mapping images obtained as a result of dividing each of three mapping images of the unripe, underripe and ripe bunches F into three hierarchical layers I, II and III.

Referring to FIG. 23, the three mapping images on the unripe, underripe and ripe bunches F shown in portions (d) of FIG. 22A, FIG. 22B and FIG. 22C are each divided into the three hierarchical layer levels I, II and III. FIG. 23 shows the color mapping images of the respective hierarchical layer levels. As shown in FIG. 23, regarding the color mapping images of the hierarchical layer level I, the density of the pixels is highest in the color mapping image on the unripe bunch F and lowest in the color mapping image on the ripe bunch F. Regarding the color mapping images of the hierarchical layer level II, the density of the pixels is highest in the color mapping image on the underripe bunch F and lowest in the color mapping image on the unripe bunch F. Regarding the color mapping images of the hierarchical layer level III, the density of the pixels is highest in the color mapping image on the ripe bunch F and lowest in the color mapping image on the unripe bunch F.

The pixel distribution corresponds to the area size ratio AR of the intensity distribution of the near infrared light obtained on the basis of the predetermined reference value and in consideration of the intensity distribution of the blue light for each hierarchical layer level. Specifically, the area size ratio AR is the ratio of the number of pixels having a quotient value fulfilling a condition for the reference value among pixels as targets of division, with respect to the number of the plurality of first pixels. For example, the pixel unit shown in FIG. 5 is subjected to division computation on a pixel-by-pixel basis by use of the pixel values of the pixel 221C and the pixel 221D that are associated with each other. The number of the pixels that are the targets of division typically matches the number of the plurality of first pixels. For example, in the case where one pixel unit includes three pixels 221C including the IR filter and one pixel 221D including the B filter, the pixel value NIRS of each of the three pixels 221C may be divided by the pixel value BLUS of the pixel 221D.

For example, the lower limit of the reference value (lower-limit threshold value) and the upper limit of the reference value (upper-limit threshold value) used for the hierarchical layer level I are respectively 60 and 70. The lower limit and the upper limit of the reference value used for the hierarchical layer level II are respectively 70 and 80. The lower limit of the reference value used for the hierarchical layer level III is 80. The upper limit is not set. An appropriate reference value may be set, so that the maturity level of the bunch F is determined based on the density of the pixels, namely, the area size ratio AR.

Figure 24:
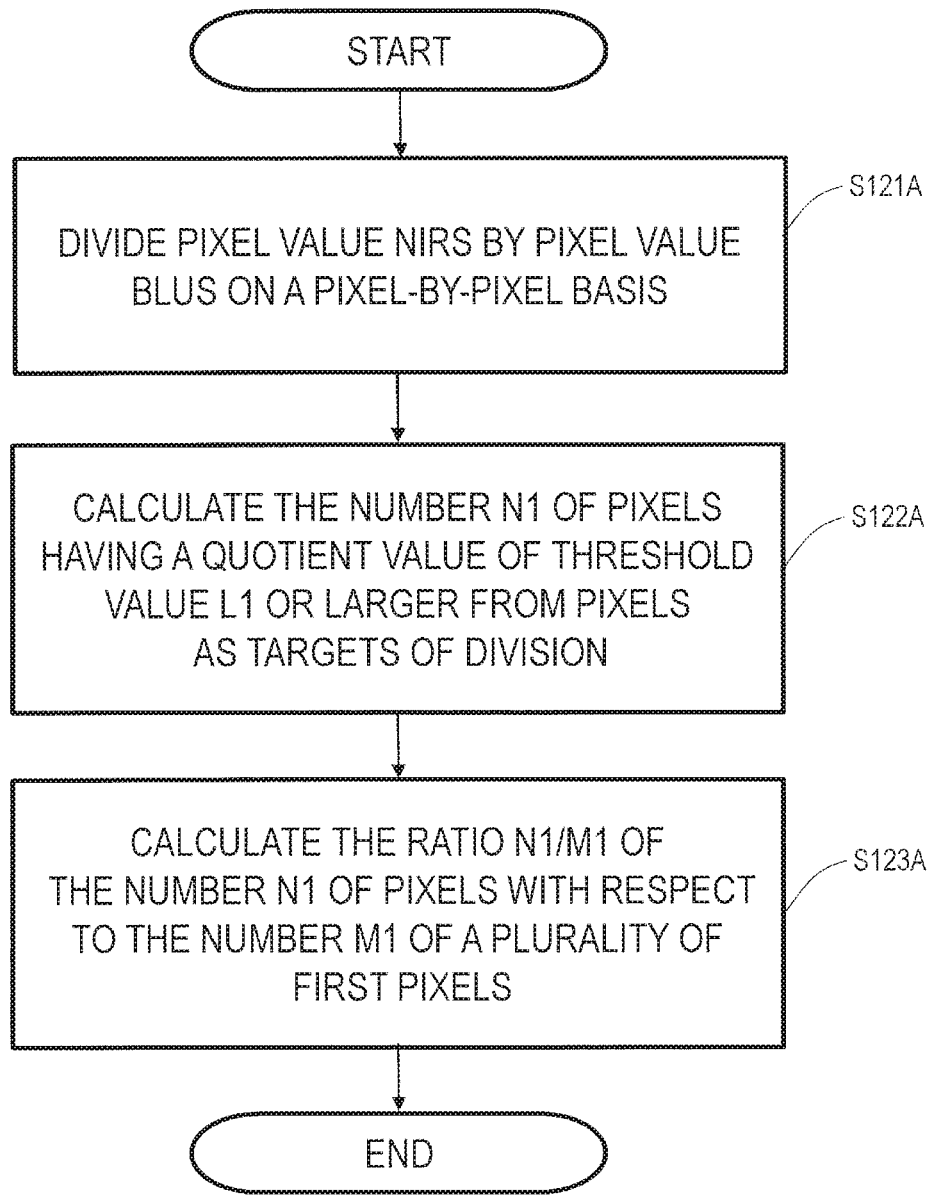
FIG. 24 is a flowchart showing a specific processing procedure of calculating an area size ratio AR in step S120A.

FIG. 24 shows a specific processing procedure of calculating the area size ratio AR in step S120A in detail. The signal processing circuit 120 finds the area size ratio AR of the intensity distribution of the near infrared light on the basis of the predetermined reference value and in consideration of the intensity distribution of the blue light. Specifically, in step S121A, the signal processing circuit 120 divides the pixel values NIRS obtained from the plurality of first pixels included in the image I by the pixel values BLUS obtained from the plurality of second pixels associated with the plurality of first pixels on a pixel-by-pixel basis.

The influence of the sunlight on the maturity level determination may keep on varying at each determination (i.e., at each image capturing operation). Therefore, a standard white plate is conventionally necessary in order to remove the influence. With the maturity level determination method in this embodiment, the pixel value NIRS is divided by the pixel value BLUS. As a result, the influence of the sunlight is suppressed and thus the standard white plate is not necessary. This simplifies the maturity level determination process.

The spectral characteristics of the standard white plate are different from the spectral characteristics of the light reflected by the bunch F. Therefore, in the case where the influence of the sunlight is removed by use of the standard white plate, the maturity level determination result may include the difference between the spectral characteristics of the standard white plate and the spectral characteristics of the reflected light as a determination error. With the maturity level determination in this embodiment, the standard white plate is not used, but the pixel value NIRS is divided by the pixel value BLUS. Therefore, the maturity level is determined with high precision.

In step S122A, the signal processing circuit 120 calculates the number N1 of pixels having a quotient value larger than, or equal to, the threshold value L1 among the pixels that are the targets of division. The number of the pixels that are the targets of division typically matches the number M1 of the plurality of first pixels. For example, for the hierarchical layer level III shown in FIG. 23, "80" may be set as the threshold value L1. Namely, as a result of computation, the number of the pixels having a pixel value (i.e., quotient value) of "80" or larger is N1. Alternatively, N1 may be the number of pixels having a quotient value smaller than, or equal to, the threshold value L1, and in step S121A, the signal processing circuit 120 may calculate the number N1 among the pixels that are the targets of division.

In step S123A, the signal processing circuit 120 finds the ratio N1/M1, namely, the ratio the calculated number N1 of the pixels with respect to the number M1 of the plurality of first pixels (or the number of the pixels that are the targets of division). The signal processing circuit 120 may generate a color mapping image in correspondence with each of the hierarchical layer levels based on the ratio N1/M1.

Now, FIG. 17 and FIG. 21 will be referred to again.

The signal processing circuit 120 generates maturity level determination information in accordance with the area size ratio AR (step S130A). Specifically, the signal processing circuit 120 generates the maturity level determination information in accordance with a result of comparing the ratio N1/M1 against the threshold value R1.

Like in embodiment 1, the signal processing circuit 120 determines whether the ratio N1/M1 calculated for the hierarchical layer level III is larger than the threshold value R1 or not. In the case where, the ratio N1/M1 is larger than the threshold value R1 in step S131 in FIG. 17, the signal processing circuit 120 generates maturity level determination information representing "ripe" (step S132). In the case where the ratio N1/M1 is smaller than, or equal to, the threshold value R1, the signal processing circuit 120 generates maturity level determination information representing, for example, "not ripe". The signal processing circuit 120 may follow the procedure described in embodiment 1 to generate maturity level determination information representing "underripe" or "unripe".

In this embodiment, the pixel value NIRS is divided by the pixel value BLUS. Thus, the maturity level is determined with high precision with the influence of the sunlight being suppressed with no use of the standard white plate. The timing to harvest the oil palm is determined highly precisely without decreasing the efficiency of the harvesting work. Therefore, the content of oil in the oil palm is increased.

(Embodiment 3)

Unlike in the harvesting apparatus 1000 in embodiment 1 or in the harvesting apparatus 1000A in embodiment 2, in a harvesting apparatus 1000B in this embodiment, when the lever L is pulled, power is supplied from the power source 300 to the harvesting means 600. Hereinafter, a structure and an operation of the harvesting apparatus 1000B will be described mainly regarding the differences from the harvesting apparatus 1000 or 1000A.

[Structure of the Harvesting Apparatus 1000B]

Figure 25:
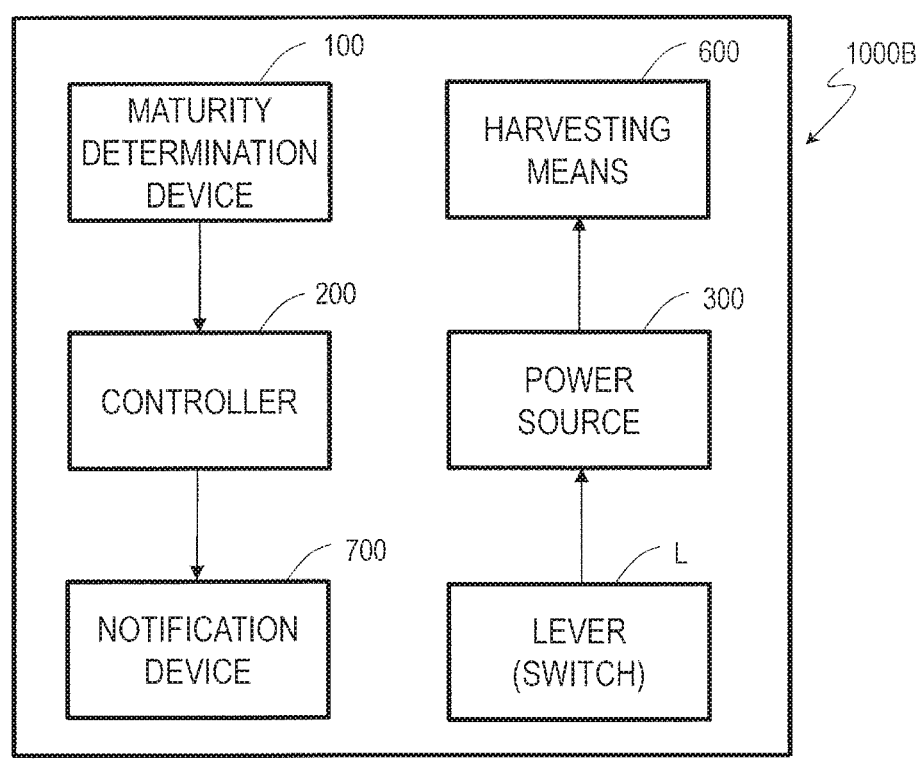
FIG. 25 is a block diagram schematically showing an example of hardware structure of a harvesting apparatus 1000B in embodiment 3.

FIG. 25 schematically shows an example of hardware structure of the harvesting apparatus 1000B in this embodiment. As shown in FIG. 25, the controller 200 does not determine whether or not to permit the harvesting means 600 to be driven in accordance with the determination result on the maturity level. According to this structure, when the harvesting worker pulls the lever L, the power is supplied from the power source 300 to the harvesting means 600 in response to the action of pulling, and thus the harvesting means 600 is driven. The notification device 700 may be a smartphone or a tablet externally connectable with the harvesting apparatus 1000B as described above.

[Operation of the Harvesting Apparatus 1000B]

Figure 26:
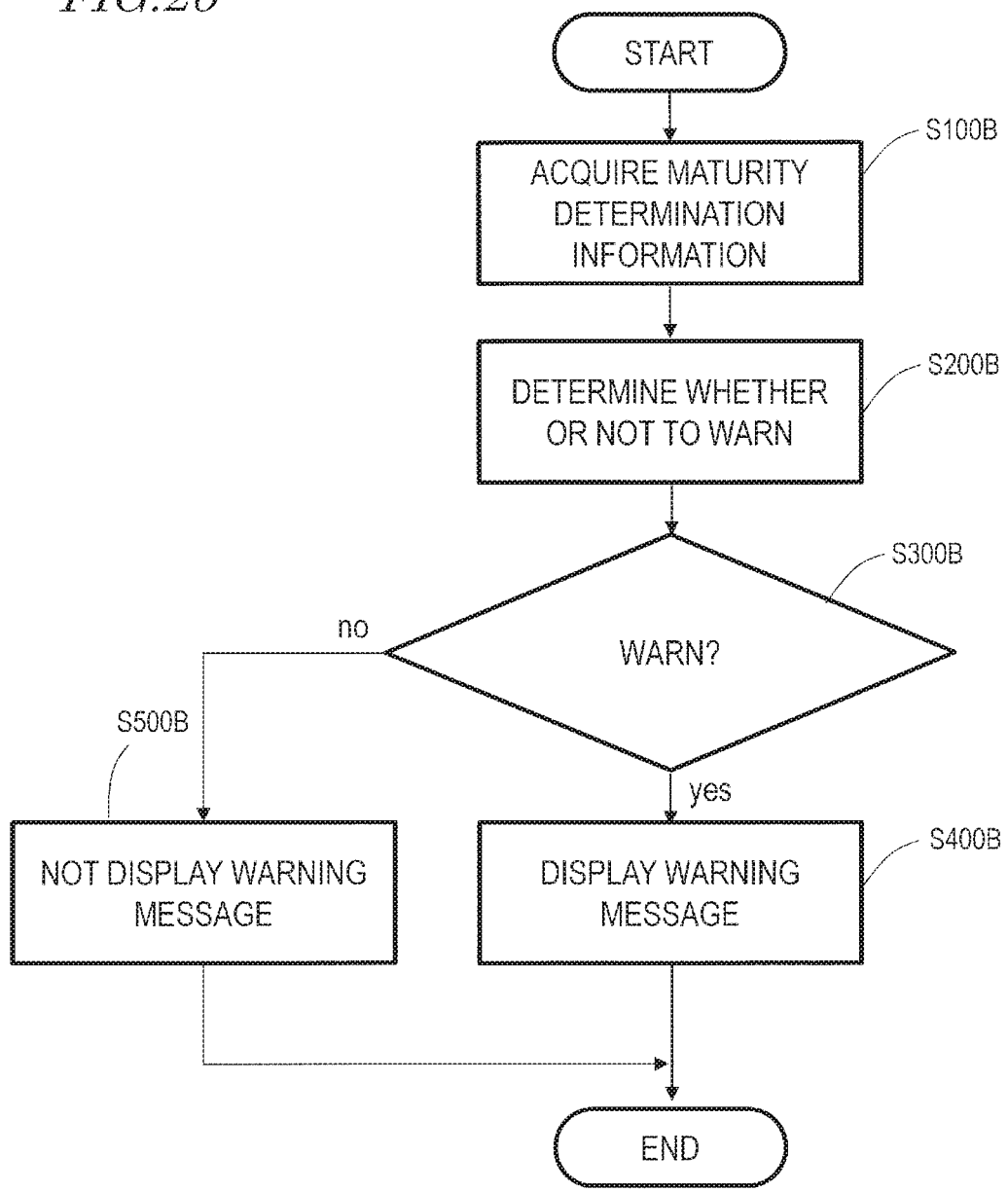
FIG. 26 is a flowchart showing an example of operation procedure of the harvesting apparatus 1000B in embodiment 3.

FIG. 26 shows an example of operation process of the harvesting apparatus 1000B in this embodiment.

The harvesting apparatus 1000B may be operated in accordance with the operation process shown in FIG. 26. The operation procedure corresponds to a harvesting method for which the harvesting apparatus 1000B is usable.

For example, the harvesting worker may direct the image capturing module 110 of the harvesting apparatus 1000B toward the bunch F and capture an image of the bunch F to obtain a maturity level determination result based on the maturity level determination described in each of embodiment 1 and embodiment 2 (step S100B). The result is notified to the harvesting worker. The maturity level determination result may be displayed on, for example, a display of a smartphone held by the harvesting worker as, for example, letter information of "ripe". The harvesting worker may acquire the maturity level determination result from the letter information. As described above, the maturity determination device 100 may determine whether the bunch F is harvestable or not based on the maturity level determination result. The harvesting worker may acquire the determination result on whether the bunch F is harvestable or not based on the information displayed on the display of the smartphone on whether the bunch F is harvestable or not.

The harvesting worker determines whether or not to operate the harvesting means 600 based on the maturity level determination result. For example, when confirming the message on the display of the smartphone that the bunch F may be harvestable, the harvesting worker may determine to drive the harvesting means 600. Based on the determination, the harvesting worker may pull the lever L to drive the harvesting means 600. In this manner, the bunch F to be harvested is harvested at the timing to harvest. By contrast, when confirming the message on the display of the smartphone that the bunch F should not be harvested, the harvesting worker may determine not to drive the harvesting means 600. In this case, based on the determination, the harvesting worker should not pull the lever L. Thus, the bunch F not to be harvested is prevented from being harvested.

For example, in step S200B, the controller 200 may determine whether or not to warn the harvesting worker regarding the harvesting of the bunch F in accordance with the maturity level determination information provided by the maturity determination device 100. For example, in the case where the maturity level determination information represents "ripe", the controller 200 determines not to warn. In the case where the maturity level determination information represents "unripe", the controller 200 determines to warn. In the case where information indicating whether the bunch F is harvestable or not indicates that the bunch F is "harvestable", the controller 200 may determine not to warn. In the case where such information indicates that the bunch F is "not harvestable", the controller 200 may determine to warn.

In the case where, for example, determining to warn in step S300B, the controller 200 determines to warn the harvesting worker that the bunch F should not be harvested (step S400B). The warning may be provided by, for example, a sound provided by a speaker of the smartphone and/or display of a warning message. By contrast, in the case where determining not to warn, the controller 200 determines not to provide such a warning sound, such a warning message or the like (step S500B). Alternatively, the controller 200 may display a message that the bunch F may be harvested.

The harvesting apparatus 1000B may include an electric current generation section (not shown) provided in the handle 400. The electric current generation section generates an electric current that causes a human body to feel hurt but is harmless to the human body. For example, in the case where a warning message that the bunch F should not be harvested but the harvesting worker does not follow the warning and pulls the lever L in an attempt to drive the harvesting means 600, the electric current generation section may sense this action and generate and output an electric current. Thus, the harvesting worker feels hurt and is expected to follow the warning in the future. The provision of the electric current also prevents the bunch F not to be harvested from being harvested by a human error.

The controller 200 may generates use history information representing a use history of the harvesting apparatus 1000B. The use history information includes information on, for example, the number of times the harvesting worker pulled the lever L to drive the harvesting means 600 despite the message that the bunch F should not be harvested, the date/time when this action occurred. The use history information is stored on, for example, an internal ROM.

The administrator may check the use history when necessary to grasp the date/time when the bunch F was erroneously harvested. Thus, the administrator may appropriately guide the harvesting worker who does not follow the warning. As a result, the erroneous harvesting of the harvesting worker is decreased. Such a direct guidance from the administrator is expected to have a psychological effect on the harvesting worker such that he/she will pay more attention to the harvesting work.

With the harvesting apparatus 1000B in this embodiment, a warning is made to the harvesting worker regarding the harvesting work, so that the bunch F to be harvested is harvested at the timing to harvest without decreasing the efficiency of the harvesting work. The bunch F not to be harvested is prevented from being harvested by a human error. As a result, the content of oil in the oil palm is increased.

A part of the maturity determination device 100 may be realized by an LSI as one chip. Each of the functional blocks of the signal processing circuit 120 may be independently a chip. Alternatively, a part of, or the entirety of, the functional blocks of the signal processing circuit 120 may be integrated into a chip. The semiconductor integrated circuit may be, for example, an application specific integrated circuit (ASIC) or a field programmable gate array (FPGA). In the case where a technology of an integrated circuit usable as a substitute of the LSI emerges by the advancement of the semiconductor technology, an integrated circuit realized by such a technology is usable.

In embodiments 1 through 3 described above, the determination method is described regarding an oil palm bunch as an example of fruit or vegetable product, which is a harvesting target. The fruit or vegetable product targeted by the present invention is not limited to the oil palm bunch, and may be any fruit or vegetable product having a reflectance characteristic of the near infrared light that the reflectance varies in accordance with the maturity level. An example of such a fruit or vegetable product is, for example, green apple or mango.

Figure 27A:
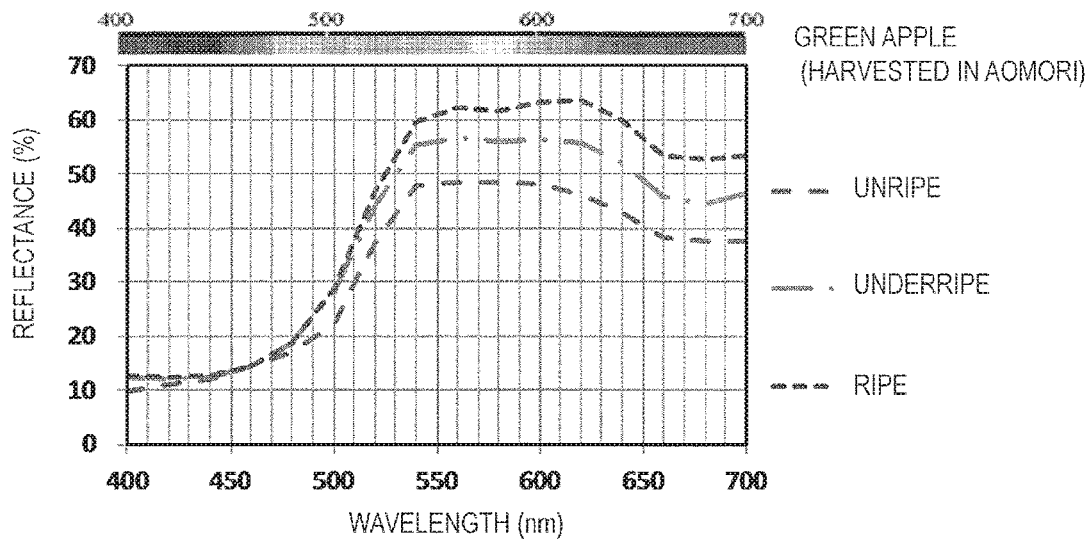
FIG. 27A is a graph showing an example of wavelength dependence of the reflectance of light reflected by green apple.
Figure 27B:
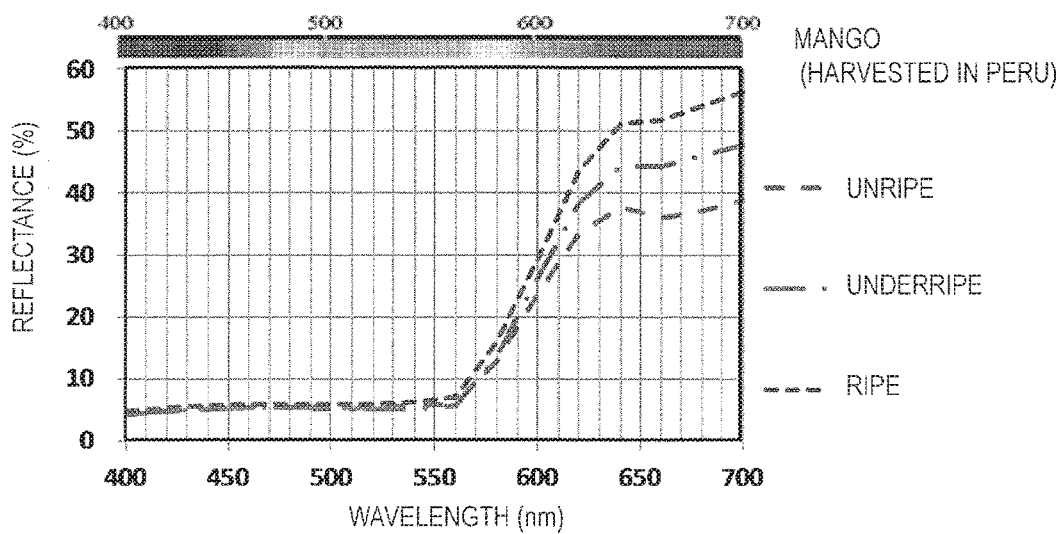
FIG. 27B is a graph showing an example of wavelength dependence of the reflectance of light reflected by mango.

FIG. 27A shows an example of wavelength dependence of the reflectance of light by green apple. FIG. 27B shows an example of wavelength dependence of the reflectance of light by mango. The horizontal axis represents the wavelength (nm) of the light, and the vertical axis represents the reflectance (%). Like in the case of the oil palm bunch F, the reflectance tends to increase as the maturity level rises especially in the wavelength band of the red light. It is seen that also in the wavelength band of the near infrared light, the reflectance tends to increase as the maturity level rises. Therefore, an embodiment of the present invention is preferably applicable to green apple and mango. Substantially the same effects are provided as for the oil palm bunch F. The target of determination of an embodiment of the present invention is not limited to the maturity level, and may be any of other indexes by which the time to harvest may be learned (e.g., growing degree, freshness, harvest level, etc.).

The harvesting method in an embodiment according to the present invention may be realized by a computer program. The computer program is configured to realize the various functions described above in embodiments 1 through 3. The computer program controls, for example, the controller 200 and the controller C of the maturity determination device 100. Information handled by these devices is temporarily stored on the RAM when being processed, and then is stored on any of various ROMs or HDDs. The CPU reads the information when necessary, and corrects the information or write additional data on the information. The storage medium storing the computer program may be, for example, a semiconductor storage medium (e.g., ROM, nonvolatile memory card, etc.), an optical storage medium (e.g., DVD, MO, MD, CD, BD, etc.), a magnetic storage medium (e.g., magnetic tape, flexible disc, etc.) or the like. Each of the functions described above in embodiments 1 through 5 is realized by the CPU loading and executing the computer program. Alternatively, each of the functions described above in embodiments 1 through 5 may be realized by the CPU in cooperation with an operating system, another application program or the like in accordance with an instruction of the computer program.

The computer program may be stored on a portable storage medium, so that the contents thereof are distributed in the market. Alternatively, the computer program may be transferred to a server computer connected via a network such as the Internet or the like, so that the contents thereof are distributed in the market. In this case, the storage device included in the server computer is encompassed in the present invention. Each of the functions described above in embodiments 1 through 5 may be stored on a computer-readable medium, or transferred, as at least one command group or a code. The "computer-readable storage medium" encompasses a communication medium including a medium assisting the computer program be carried from one site to another site and also encompasses a computer storage medium. The storage medium may be any commercially available medium accessible by a general-purpose computer or a special-purpose computer.

In this specification, various illustrative elements, blocks, modules, circuits and steps are described generally regarding the functionality thereof in order to clearly show the synonymy between hardware and software. Whether such functionality is implemented as hardware or software depends on the designing restriction imposed on each of applications and the entire system. A person of ordinary skill in the art could implement the functions by any of various methods for specific applications, but determination on such implementation should not be construed as departing from the scope of this disclosure.

Various illustrative logical blocks and processing units described in relation with the disclosure of this specification may be implemented or executed by a general-purpose processor, a digital signal processor (DSP), an ASIC, an FPGA, any other programmable logical device, a discrete gate or transistor logic, or a discrete hardware component designed to execute the functions described in this specification, or a combination of any of these. The general-purpose processor may be a microprocessor, or may be a conventional processor, controller, microcontroller or state machine. The processor may be implemented by a combination of computing devices. For example, the processor may be realized by a combination of a DSP and a microprocessor, a combination of a plurality of microprocessors, a combination of a DSP core and at least one microprocessor connected with the DSP core, or a combination of any other such devices.

The determination methods or the steps of algorithm described in relation with the disclosure of this specification may be directly embodied by a software module executable by hardware (especially, a processor) or by a combination of hardware and the software module. The software module may be present in a RAM, a flash memory, a ROM, an EPROM, an EEPROM, a register, a hard disc, a removable disc, a CD-ROM, or any storage medium in any form known in this field. A typical storage medium may be coupled to the processor such that information may be read therefrom, or written thereto, by the processor. With another method, the storage medium may be integrated with the processor. The processor and the storage medium may be in the ASIC. The ASIC may be mounted on the harvesting apparatus. Alternatively, the processor and the storage medium may be housed in the harvesting apparatus as discrete elements.

Embodiments of the present invention have been described in detail with reference to the drawings. Specific structures are not limited to any of the embodiments, and designs and the like not departing from the gist of the present invention are encompassed in the scope of the claims.

A harvesting apparatus and a harvesting method in an embodiment according to the present invention are preferably usable for harvesting a fruit or vegetable product.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A method for harvesting a fruit or vegetable product using a harvesting apparatus including a maturity determination device that determines a maturity level of the fruit or vegetable product and a harvester that harvests the fruit or vegetable product, the method comprising the steps of:
   determining the maturity level of the fruit or vegetable product by the maturity determination device to acquire a determination result on the maturity level, and determining whether the fruit or vegetable product is harvestable or not based on the determination result on the maturity level to acquire a determination result on whether the fruit or vegetable product is harvestable or not;
   determining an operation of the harvester based on the determination result on the maturity level;
   harvesting the fruit or vegetable product based on the determination on the operation of the harvester; and
   notifying, by using a notification device, a user of the harvesting apparatus of whether the fruit or vegetable product is harvestable or not based on the determination result on whether the fruit or vegetable product is harvestable or not.

2. The method according to claim 1, wherein:
   in a case where the determination result on the maturity level indicates that the maturity level has reached a predetermined level in the step of acquiring the determination result on the maturity level, a determination is made to permit the harvester to be operated in the step of determining the operation of the harvester; and
   in a case where the determination result on the maturity level indicates that the maturity level has not reached the predetermined level in the step of acquiring the determination result on the maturity level, a determination is made not to permit the harvester to be operated in the step of determining the operation of the harvester.

3. The method according to claim 1, further comprising the step of notifying, by using a notification device, a user of the harvesting apparatus of the maturity level based on the determination result on the maturity level.

4. The method according to claim 1, further comprising a step of capturing an image of an entirety of the fruit or vegetable product to obtain information on the fruit or vegetable product and trimming the captured image to provide an extracted image portion that is used to determine the maturity level of the fruit or vegetable product.

5. The method according to claim 1, further comprising the step of, in a case where the fruit or vegetable product is determined as not being harvestable in the step of acquiring the determination result on the maturity level, warning a user of the harvesting apparatus that the fruit or vegetable product should not be harvested.

6. The method according to claim 5, in the step of determining the operation of the harvester, a determination is made not to permit the harvester to be operated, as well as said warning the user of the harvesting apparatus that the fruit or vegetable product should not be harvested.

7. The method according to claim 1, further comprising the step of outputting maturity level determination information including the determination result on the maturity level.

8. The method according to claim 1, further comprising the step of printing maturity level determination information including the determination result on the maturity level.

9. The method according to claim 1, further comprising the step of generating use history information representing a use history of the harvesting apparatus.

10. The method according to claim 1, wherein the step of acquiring the determination result on the maturity level includes the steps of:

receiving an image including at least a part of the fruit or vegetable product, the image including at least an intensity distribution of light of a first wavelength band, an intensity of the light of the first wavelength band reflected by the fruit or vegetable product varying in accordance with the maturity level;

finding an area size ratio of the intensity distribution of the light of the first wavelength band on the basis of a predetermined reference value; and determining the maturity level in accordance with the area size ratio to acquire the determination result on the maturity level.

11. The method according to claim 1, wherein the step of acquiring the determination result on the maturity level includes the steps of:

receiving an image including at least a part of the fruit or vegetable product, the image including at least an intensity distribution of light of a first wavelength band and an intensity distribution of light of a second wavelength band, an intensity of the light of the first wavelength band reflected by the fruit or vegetable product varying in accordance with the maturity level, and an intensity of the light of the second wavelength band reflected by the fruit or vegetable product being generally constant regardless of the maturity level;

finding an area size ratio of the intensity distribution of the light of the first wavelength band on the basis of a predetermined reference value and in consideration of the intensity distribution of the light of the second wavelength band; and determining the maturity level in accordance with the area size ratio to acquire the determination result on the maturity level.

12. The method according to claim 10, wherein the step of acquiring the determination result on the maturity level further includes the step of capturing an image of at least a part of the fruit or vegetable product to acquire the image data.

13. The method according to claim 1, wherein the fruit or vegetable product is a bunch with a large number of fruits.

14. A harvesting apparatus for a fruit or vegetable product, comprising:

a maturity determination device that determines a maturity level of the fruit or vegetable product;

a harvester that harvests the fruit or vegetable product;

a power source generator that generates power to drive the harvester; and a controller that determines whether or not to supply the power to the harvester based on a determination result on the maturity level provided by the maturity determination device; and a notification device; wherein the maturity determination device determines whether the fruit or vegetable product is harvestable or not based on the determination result on the maturity level; and the notification device notifies a user of the harvesting apparatus of whether the fruit or vegetable product is harvestable or not based on a determination result on whether the fruit or vegetable product is harvestable or not.

15. The harvesting apparatus according to claim 14, wherein the maturity determination device comprises:

an image capturing module that captures an image of an entirety of the fruit or vegetable product and obtains information on the fruit or vegetable product; and a signal processing circuit that trims the captured image to provide an extracted image portion that is used to determine the maturity level of the fruit or vegetable product.

16. A method for harvesting a fruit or vegetable product using a harvesting apparatus including a maturity determination device that determines a maturity level of the fruit or vegetable product and a harvester that harvests the fruit or vegetable product, the method comprising the steps of:

determining the maturity level of the fruit or vegetable product by the maturity determination device to acquire a determination result on the maturity level;

determining an operation of the harvester based on the determination result on the maturity level; and harvesting the fruit or vegetable product based on the determination on the operation of the harvester; wherein the step of acquiring the determination result on the maturity level includes the steps of:

receiving an image including at least a part of the fruit or vegetable product, the image including at least an intensity distribution of light of a first wavelength band, an intensity of the light of the first wavelength band reflected by the fruit or vegetable product varying in accordance with the maturity level;

finding an area size ratio of the intensity distribution of the light of the first wavelength band on the basis of a predetermined reference value; and determining the maturity level in accordance with the area size ratio to acquire the determination result on the maturity level.

* * * * *